US012806256B2

(12) United States Patent
Zhu et al.

(10) Patent No.: US 12,806,256 B2
(45) Date of Patent: Nov. 24, 2026

(54) GPC3-BINDING APTAMER CHIMERA AND METHOD OF USE THEREOF TO STIMULATE AN IMMUNE RESPONSE IN A TUMOR TISSUE

(71) Applicant: Guardian Therapeutics, LLC, Lexington, MA (US)

(72) Inventors: Shuhao Zhu, Concord, MA (US); Kristin Thompson, Arlington, MA (US); Christina McGuire, Somerville, MA (US); Jin Yuan, North Andover, MA (US)

(73) Assignee: GUARDIAN THERAPEUTICS, LLC, Lexington, MA (US)

( * ) Notice: Subject to any disclaimer, the term of this patent is extended or adjusted under 35 U.S.C. 154(b) by 712 days.

(21) Appl. No.: 18/252,763

(22) PCT Filed: Nov. 12, 2021

(86) PCT No.: PCT/US2021/059062

§ 371 (c)(1),
(2) Date: May 12, 2023

(87) PCT Pub. No.: WO2022/104006

PCT Pub. Date: May 19, 2022

(65) Prior Publication Data

US 2025/0281621 A1 Sep. 11, 2025

Related U.S. Application Data

(60) Provisional application No. 63/113,640, filed on Nov. 13, 2020.

(51) Int. Cl.

| | |
|---|---|
| ***A61K 39/00*** | (2006.01) |
| ***A61K 47/54*** | (2017.01) |
| ***A61P 35/00*** | (2006.01) |
| ***C12N 15/115*** | (2010.01) |
| ***C12N 15/117*** | (2010.01) |

(52) U.S. Cl.

CPC .... *A61K 39/001174* (2018.08); *A61K 47/549* (2017.08); *A61P 35/00* (2018.01); *C12N 15/115* (2013.01); *C12N 15/117* (2013.01); *C12N 2310/16* (2013.01); *C12N 2310/321* (2013.01); *C12N 2310/3519* (2013.01); *C12N 2320/30* (2013.01)

(58) Field of Classification Search

CPC ........ A61K 39/001174; A61K 39/0005; A61K 47/549; A61K 2039/515; A61K 2039/545; A61K 2039/585; A61K 31/535; A61K 31/7105; A61P 35/00; A61P 1/16; C12N 15/115; C12N 15/117; C12N 2310/16; C12N 2310/321; C12N 2310/3519; C12N 2310/351; C12N 2310/17; C12N 2310/15; C12N 2320/30; C12N 2320/13

See application file for complete search history.

(56) References Cited

U.S. PATENT DOCUMENTS

| | | | |
|---|---|---|---|
| 3,687,808 | A | 8/1972 | Merigan et al. |
| 5,270,163 | A | 12/1993 | Gold et al. |
| 5,475,096 | A | 12/1995 | Gold et al. |
| 6,207,646 | B1 | 3/2001 | Krieg et al. |
| 6,214,806 | B1 | 4/2001 | Krieg et al. |
| 6,239,116 | B1 | 5/2001 | Krieg et al. |
| 6,406,705 | B1 | 6/2002 | Davis et al. |
| 6,653,292 | B1 | 11/2003 | Krieg et al. |
| 7,087,735 | B2 | 8/2006 | Gold |
| 7,662,949 | B2 | 2/2010 | Forsbach et al. |
| 8,128,944 | B2 | 3/2012 | Jurk et al. |
| 8,153,141 | B2 | 4/2012 | Lipford et al. |
| 8,354,522 | B2 | 1/2013 | Forsbach et al. |
| 8,552,165 | B2 | 10/2013 | Davis et al. |
| 8,580,268 | B2 | 11/2013 | Debelak et al. |
| 8,834,900 | B2 | 9/2014 | Krieg et al. |
| 9,205,143 | B2 | 12/2015 | Davis et al. |
| 9,382,545 | B2 | 7/2016 | Debelak et al. |
| 9,453,059 | B2 | 9/2016 | Davis et al. |
| 10,260,071 | B2 | 4/2019 | Debelak et al. |
| 2004/0253679 | A1 | 12/2004 | Epstein et al. |
| 2005/0124565 | A1 | 6/2005 | Diener et al. |
| 2009/0060907 | A1 | 3/2009 | Aburatani et al. |
| 2009/0081679 | A1 | 3/2009 | Keefe et al. |
| 2019/0136239 | A1 | 5/2019 | Oh et al. |
| 2019/0241633 | A1 | 8/2019 | Fotin-mleczek et al. |

FOREIGN PATENT DOCUMENTS

| | | | |
|---|---|---|---|
| WO | 9837919 | A1 | 9/1998 |
| WO | 2004035763 | A2 | 4/2004 |
| WO | 2006050498 | A2 | 5/2006 |

OTHER PUBLICATIONS

Hasegawa et al. Methods for Improving Aptamer Binding Affinity. Molecules 2016, 21, 421; doi:10.3390/molecules21040421 (Year: 2016).*

Park et al. Targeted Therapy of Hepatocellular Carcinoma Using Gemcitabine-Incorporated GPC3 Aptamer. Pharmaceutics 2020, 12, 985; doi:10.3390/pharmaceutics12100985. (Year: 2020).*

Keefe, Anthony D. et al., "SELEX with modified nucleotides", Current Opinion in Chemical Biology, Current Biology Ltd, London, GB, vol. 12, No. 4, Aug. 1, 2008, pp. 448-456 (9 pages).

Zhang, Liqin et al., "Aptamers against Cells Overexpressing Glypican 3 from Expanded Genetic Systems Combined with Cell Engineering and Laboratory Evolution", Angewandte Chemie, Verlag Chemie, Hoboken, USA, vol. 55, No. 40, Sep. 7, 2016, pp. 12372-12375 (4 pages).

"EASL Clinical Practice Guidelines: Management of hepatocellular carcinoma", Journal of Hepatology, vol. 69, No. 1, Jul. 2018, pp. 182-236, DOI: 10.1016/j.jhep.2018.03.019, (55 pages).

(Continued)

*Primary Examiner* — Robert S Landsman
(74) *Attorney, Agent, or Firm* — Proskauer Rose LLP

(57) ABSTRACT

The present disclosure relates to GPC3 aptamers. GPC3 aptamer conjugates and compositions, and use thereof. In particular, the present disclosure develops GPC3-specific aptamer-drug conjugates for targeted cancer therapy.

14 Claims, 9 Drawing Sheets

Specification includes a Sequence Listing.

(56) References Cited

OTHER PUBLICATIONS

Chen, Cheng, et al., "Development of T cells carrying two complementary chimeric antigen receptors against glypican-3 and asialoglycoprotein receptor 1 for the treatment of hepatocellular carcinoma", Cancer Immunology, Immunotherapy, vol. 66, No. 4, 2017, pp. 475-489, DOI: 10.1007/s00262-016-1949-8, (15 pages).
Ellington, Andrew D., et al., "In vitro selection of RNA molecules that bind specific ligands", Nature, vol. 346, 1990, pp. 818-822, DOI: 10.1038/346818a0, (5 pages).
Englisch, Uwe, et al., "Chemically Modified Oligonucleotides as Probes and Inhibitors", Angewandte Chemie International Edition, vol. 30, No. 6, Jun. 1991, pp. 613-629, DOI: 10.1002/anie.199106133, (17 pages).
Feng, Mingqian, et al., "Therapeutically targeting glypican-3 via a conformation-specific single-domain antibody in hepatocellular carcinoma", Proceedings of the National Academy of Sciences, vol. 110, No. 12, 2013, pp. E1083-E1091, DOI: 10.1073/pnas.1217868110, (9 pages).
Fu, Ying, et al., "Glypican-3-Specific Antibody Drug Conjugates Targeting Hepatocellular Carcinoma", Hepatology, vol. 70, No. 2, Aug. 2019, pp. 563-576, DOI: 10.1002/hep.30326, Author Manuscript (21 pages).
Gao, Wei, et al., "Human Monoclonal Antibody Targeting the Heparan Sulfate Chains of Glypican-3 Inhibits HGF-Mediated Migration and Motility of Hepatocellular Carcinoma Cells", PLoS One, vol. 10, No. 9, 2015, DOI: 10.1371/journal.pone.0137664, (13 pages).
Gao, Wei, et al., "Inactivation of Wnt signaling by a human antibody that recognizes the heparan sulfate chains of glypican-3 for liver cancer therapy", Hepatology, vol. 60, No. 2, Aug. 2014, pp. 576-587, DOI: 10.1002/hep.26996, (12 pages).
Hanaoka, Hirofumi, et al., "Glypican-3 targeted human heavy chain antibody as a drug carrier for hepatocellular carcinoma therapy", Molecular Pharmaceutics, vol. 12, No. 6, 2015, pp. 2151-2157, DOI: 10.1021/acs.molpharmaceut.5b00132, Author Manuscript (15 pages).
Iglesias, Bibiana V., et al., "Expression pattern of glypican-3 (GPC3) during human embryonic and fetal development", Histology and Histopathology, vol. 23, 2008, pp. 1333-1340, DOI: 10.14670/HH-23.1333, (8 pages).
International Preliminary Report on Patentability, Ch. I, for PCT/US2021/059062 dated May 25, 2023 (8 pages).
International Search Report and Written Opinion for PCT/US2021/059062 dated May 11, 2022 (13 pages).
Ishiguro, Takahiro, et al., "Anti-glypican 3 antibody as a potential antitumor agent for human liver cancer", Cancer Research, vol. 68, No. 23, 2008, pp. 9832-9838, DOI: 10.1158/0008-5472.CAN-08-1973, (7 pages).
Jhaveri, Sulay D., et al., "In Vitro Selection of RNA Aptamers to a Protein Target by Filter Immobilization", Current Protocols in Nucleic Acid Chemistry, 2001, DOI: 10.1002/0471142700.nc0903s00, (25 pages).
Lakshman, Mahesh K., et al., "Modified Nucleosides in Biochemistry, Biotechnology and Medicine. Edited by Piet Herdewijn.", Angewandte Chemie International Edition, vol. 48, No. 21, May 11, 2009, pp. 3734-3735, DOI: 10.1002/anie.200900932, (2 pages).
Li, Na, et al., "A Frizzled-Like Cysteine-Rich Domain in Glypican-3 Mediates Wnt Binding and Regulates Hepatocellular Carcinoma Tumor Growth in Mice", Hepatology, vol. 70, No. 4, Oct. 2019, pp. 1231-1245, DOI: 10.1002/hep.30646, Author Manuscript (24 pages).
Lin, Qiang, et al., "Expression of GPC3 protein and its significance in lung squamous cell carcinoma", Medical Oncology, vol. 29, 2012, pp. 663-669, DOI: 10.1007/s12032-011-9973-1, (7 pages).
Maeda, Daichi, et al., "Glypican-3 expression in clear cell adenocarcinoma of the ovary", Modern Pathology, vol. 22, No. 6, Jun. 2009, pp. 824-832, DOI: 10.1038/modpathol.2009.40, (9 pages).
McNamara, James O, et al., "Cell type-specific delivery of siRNAs with aptamer-siRNA chimeras", Nature Biotechnology, vol. 24, 2006, pp. 1005-1015, DOI: 10.1038/nbt1223, (11 pages).
Mitsunaga, Makoto, et al., "Cancer cell-selective in vivo near infrared photoimmunotherapy targeting specific membrane molecules", Nature Medicine, vol. 17, No. 12, 2011, pp. 1685-1691, DOI: 10.1038/nm.2554, Author Manuscript (17 pages).
Nakano, Kiyotaka, et al., "Anti-glypican 3 antibodies cause ADCC against human hepatocellular carcinoma cells", Biochemical and Biophysical Research Communications, vol. 378, No. 2, Jan. 9, 2009, pp. 279-284, DOI: 10.1016/j.bbrc2008.11.033, (5 pages).
Nakatsura, Tetsuya, et al., "Glypican-3, overexpressed specifically in human hepatocellular carcinoma, is a novel tumor marker", Biochemical and Biophysical Research Communications, vol. 306, No. 1, Jun. 20, 2023, pp. 16-25, DOI: 10.1016/s0006-291x(03)00908-2, (10 pages).
Nishida, Takahiro, et al., "Glypican 3-Targeted Therapy in Hepatocellular Carcinoma", Cancers, vol. 11, No. 9, 2019, pp. 1339, DOI: https://doi.org/10.3390/cancers11091339, (13 pages).
Odeh, Fadwa, et al., "Aptamers Chemistry: Chemical Modifications and Conjugation Strategies", Molecules, vol. 25, No. 1, 3, 2020, DOI: 10.3390/molecules25010003, (51 pages).
Ortiz, Michael V., "Immunotherapeutic Targeting of GPC3 in Pediatric Solid Embryonal Tumors", Frontiers in Oncology, vol. 9, Article No. 108, Feb. 2019, DOI: 10.3389/fonc2019.00108, (8 pages).
Park, Jun Young, et al., "Targeted Therapy of Hepatocellular Carcinoma Using Gemcitabine-Incorporated GPC3 Aptamer", Pharmaceutics, vol. 12, No. 10, 2020, 985, DOI: 10.3390/pharmaceutics12100985, (15 pages).
Shum, Ka To, et al., "Differential Inhibitory Activities and Stabilisation of DNA Aptamers against the SARS Coronavirus Helicase", ChemBioChem, vol. 9. No. 18, Dec. 15, 2008, pp. 3037-3045, DOI: 10.1002/cbic.200800491, (9 pages).
Thiel, Kristina W., et al., "Delivery of chemo-sensitizing siRNAs to HER2+-breast cancer cells using RNA aptamers", Nucleic Acids Research, vol. 40, No. 13, Jul. 1, 2012, pp. 6319-6337, DOI: 10.1093/nar/gks294, (19 pages).
Tuerk, Craig, et al., "Systematic Evolution of Ligands by Exponential Enrichment: RNA Ligands to Bacteriophage T4 DNA Polymerase", Science, vol. 249, No. 4968, 1990, pp. 505-510, DOI: 10.1126/science.2200121, (6 pages).
Ushiku, Tetsuo, et al., "Glypican 3-expressing gastric carcinoma: Distinct subgroup unifying hepatoid, clear-cell, and α-fetoprotein-producing gastric carcinomas", Cancer Science, vol. 100, No. 4, 2009, pp. 626-632, DOI: 10.1111/j.1349-7006.2009.01108.x, (7 pages).
Wang, Chunguang, et al., "Construction of an immunotoxin, HN3-mPE24, targeting glypican-3 for liver cancer therapy", Oncotarget, vol. 8, No. 20, 2017, pp. 32450-32460, DOI: 10.18632/oncotarget.10592, (11 pages).
Zhang, Jian-Xiong, et al., "Identifying a set of influential spreaders in complex networks", Scientific Reports, vol. 6, Article No. 27823, 2016, DOI: 10.1038/srep27823, (10 pages).
Zhang, Yongdong, et al., "Preparation of a monoclonal antibody against the carcinoembryonic antigen, glypican-3", Molecular Medicine Reports, vol. 19, No. 5, 2019, pp. 3889-3895, DOI: 10.3892/mmr.2019.10019, (7 pages).
Zhou, Fubo, et al., "Glypican-3: A promising biomarker for hepatocellular carcinoma diagnosis and treatment", Medical Research Reviews, vol. 38. No. 2, Mar. 2018, pp. 741-767, DOI: 10.1002/med.21455, (17 pages).
Zhu, Guizhi, et al., "Aptamer-Drug Conjugates", Bioconjugate Chemistry, vol. 26, No. 11, 2015, pp. 2186-2197, DOI: 10.1021/acs.bioconjchem.5b00291, Author Manuscript (27 pages).

* cited by examiner

SEQUENCE LISTING

```
<160> NUMBER OF SEQ ID NOS: 83

<210> SEQ ID NO 1
<211> LENGTH: 76
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (24)..(53)
<223> OTHER INFORMATION: a, c, t, or g

<400> SEQUENCE: 1
gggagacaag aataaagcga gttnnnnnnn nnnnnnnnnn nnnnnnnnnn nnnaagagtc     60
gatgatgctt agctag                                                     76

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taatacgact cactataggg agacaagaat aaagcgagtt                           40

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctagctaagc atcatcgact ctt                                             23

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(52)
<223> OTHER INFORMATION: a, c, t, or g

<400> SEQUENCE: 4
gggagtccta cgtacagtct agnnnnnnnn nnnnnnnnnn nnnnnnnnnn nntcgatgca     60
ggatctagct atcgat                                                     76

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taatacgact cactataggg agtcctacgt acagtctag                            39

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcgatagct agatcctgca tcga 24

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (3)..(3)
<223> OTHER INFORMATION: a, c, t, or g
<220> FEATURE:
<221> NAME/KEY: misc_feature
<222> LOCATION: (3)..(3)
<223> OTHER INFORMATION: The nucleotide at this position forms a base pair with the nucleotide at position 12
<220> FEATURE:
<221> NAME/KEY: modified_base
<222> LOCATION: (12)..(12)
<223> OTHER INFORMATION: a, c, t, or g
<220> FEATURE:
<221> NAME/KEY: misc_feature
<222> LOCATION: (12)..(12)
<223> OTHER INFORMATION: The nucleotide at this position forms a base pair with the nucleotide at position 3

<400> SEQUENCE: 7
cgngttgcta cncrag 16

<210> SEQ ID NO 8
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gggagacaag aataaagcga gttgctactc aaggcacgtc gtgtgcgctg attcaagagt 60
cgatgatgct tagctag 77

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
gggagacaag aataaagcga gtttcgtgtc gtgttgctac acaagtccgt taccaagagt 60
cgatgatgct tagctag 77

<210> SEQ ID NO 10
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
gggagacaag aataaagcga gttaacgggt tgctacccaa gtcttgcaat tcgcaagagt 60
cgatgatgct tagctag 77

<210> SEQ ID NO 11
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
gggagacaag aataaagcga gttgcatgat cgtgttgcta cacgaggtct cattaagagt 60
cgatgatgct tagctag 77

<210> SEQ ID NO 12
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
gggagacaag aataaagcga gtttgaagcc attaccgggt tgctacccaa ggacaagagt 60
cgatgatgct tagctag 77

<210> SEQ ID NO 13
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
gggagacaag aataaagcga gttgttgcat cgagttgcta ctcaaggtcg cgtcaagagt 60
cgatgatgct tagctag 77

<210> SEQ ID NO 14
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
gggagacaag aataaagcga gttgcctgtt gcatcgtgtt gctacacaag attgaagagt 60
cgatgatgct tagctag 77

<210> SEQ ID NO 15
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
gggagacaag aataaagcga gttcatcgtg ttgctacaca aggactctag caccaagagt 60
cgatgatgct tagctag 77

<210> SEQ ID NO 16

<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gggagacaag aataaagcga gttgttgacg ggttgctacc cgagtcttgc attcaagagt 60
cgatgatgct tagctag 77

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gggagtccta cgtacagtct agatcgggtt gctacccaag ctgcggtaca aatcgatgca 60
ggatctagct atcgat 76

<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
gggagtccta cgtacagtct aggacgagtt gctacccaag tcccgcgttt gatcgatgca 60
ggatctagct atcgat 76

<210> SEQ ID NO 19
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
gggagtccta cgtacagtct agatcgggtt gctacccaag ctgcggttca aatcgatgca 60
ggatctagct atcgat 76

<210> SEQ ID NO 20
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
gggagtccta cgtacagtct agatcgggtt gctacccaag ctgcggttca catcgatgca 60
ggatctagct atcgat 76

<210> SEQ ID NO 21
<211> LENGTH: 76
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 21
gggagtccta cgtacagtct agatcgggtt gctacccaag ctgcggtaca gatcgatgca     60
ggatctagct atcgat                                                     76

<210> SEQ ID NO 22
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gggagtccta cgtacagtct agatcgggtt gctacccaag ctgcggttca gatcgatgca     60
ggatctagct atcgat                                                     76

<210> SEQ ID NO 23
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cgucaucggg uugcuaccca aggacaagag ucgaugacg                            39

<210> SEQ ID NO 24
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cgucaucggg uugcuaccca aggucaagag acgaugacg                            39

<210> SEQ ID NO 25
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cgucaucggg uugcuaccca aggccaggag gcgaugacg                            39

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagccattac cgggttgcta cccaaggaca agagtcgatg atgctt                    46

<210> SEQ ID NO 27
<211> LENGTH: 45

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
aagcattacc gggttgctac ccaaggacaa gagtcgatga tgctt 45

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
aagccattac cgggttgcta cccgaggaca agagtcgatg atgctt 46

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
aagccattat cgggttgcta cccaaggaca agagtcgatg atgctt 46

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
cattatcggg ttgctaccca aggacaagag tcgatgatg 39

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
cattatcggg ttgctacccg aggacaagag tcgatgatg 39

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
cgtcatcggg ttgctaccca aggacaagag tcgatgacg 39

<210> SEQ ID NO 33
<211> LENGTH: 39
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 33
cgtcgtcggg ttgctaccca aggacaagag tcgacgacg 39

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
ggcatcgggt tgctacccaa ggacaagagt cgatgcc 37

<210> SEQ ID NO 35
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
cgucaucggg uugcuaccca aggucaggug acgaugacg 39

<210> SEQ ID NO 36
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
cgucaucggg uugcuaccca aggucaggag acgaugacg 39

<210> SEQ ID NO 37
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
gggagacaag aataaagcga gttgctactc aaggcacgtc gtgtgcgctg attcaagagt 60
cgatgatgct tagctag 77

<210> SEQ ID NO 38
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
gggagacaag aataaagcga gtttcgtgtc gtgttgctac acaagtccgt taccaagagt 60
cgatgatgct tagctag 77

<210> SEQ ID NO 39
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gggagacaag aataaagcga gttaacgggt tgctacccaa gtcttgcaat tcgcaagagt     60
cgatgatgct tagctag                                                    77

<210> SEQ ID NO 40
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gggagacaag aataaagcga gttgcatgat cgtgttgcta cacgaggtct cattaagagt     60
cgatgatgct tagctag                                                    77

<210> SEQ ID NO 41
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gggagacaag aataaagcga gtttgaagcc attaccgggt tgctacccaa ggacaagagt     60
cgatgatgct tagctag                                                    77

<210> SEQ ID NO 42
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gggagacaag aataaagcga gttgttgcat cgagttgcta ctcaaggtcg cgtcaagagt     60
cgatgatgct tagctag                                                    77

<210> SEQ ID NO 43
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gggagacaag aataaagcga gttgcctgtt gcatcgtgtt gctacacaag attgaagagt     60
cgatgatgct tagctag                                                    77

<210> SEQ ID NO 44
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
gggagacaag aataaagcga gttcatcgtg ttgctacaca aggactctag caccaagagt 60
cgatgatgct tagctag 77

<210> SEQ ID NO 45
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
gggagacaag aataaagcga gttgttgacg ggttgctacc cgagtcttgc attcaagagt 60
cgatgatgct tagctag 77

<210> SEQ ID NO 46
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
gggagtccta cgtacagtct agatcgggtt gctacccaag ctgcggtaca aatcgatgca 60
ggatctagct atcgat 76

<210> SEQ ID NO 47
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
gggagtccta cgtacagtct aggacgagtt gctacccaag tcccgcgttt gatcgatgca 60
ggatctagct atcgat 76

<210> SEQ ID NO 48
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
gggagtccta cgtacagtct agatcgggtt gctacccaag ctgcggttca aatcgatgca 60
ggatctagct atcgat 76

<210> SEQ ID NO 49
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
gggagtccta cgtacagtct agatcgggtt gctacccaag ctgcggttca catcgatgca 60
ggatctagct atcgat 76

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
gggagtccta cgtacagtct agatcgggtt gctacccaag ctgcggtaca gatcgatgca 60
ggatctagct atcgat 76

<210> SEQ ID NO 51
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
gggagtccta cgtacagtct agatcgggtt gctacccaag ctgcggttca gatcgatgca 60
ggatctagct atcgat 76

<210> SEQ ID NO 52
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
cgucaucggg uugcuaccca aggacaagag ucgaugacg 39

<210> SEQ ID NO 53
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
cgucaucggg uugcuaccca aggucaagag acgaugacg 39

<210> SEQ ID NO 54
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54
cgucaucggg uugcuaccca aggccaggag gcgaugacg 39

<210> SEQ ID NO 55
<211> LENGTH: 46
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 55
aagccattac cgggttgcta cccaaggaca agagtcgatg atgctt 46

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aagcattacc gggttgctac ccaaggacaa gagtcgatga tgctt 45

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aagccattac cgggttgcta cccgaggaca agagtcgatg atgctt 46

<210> SEQ ID NO 58
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aagccattat cgggttgcta cccaaggaca agagtcgatg atgctt 46

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cattatcggg ttgctaccca aggacaagag tcgatgatg 39

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cattatcggg ttgctacccg aggacaagag tcgatgatg 39

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
cgtcatcggg ttgctaccca aggacaagag tcgatgacg 39

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
cgtcgtcggg ttgctaccca aggacaagag tcgacgacg 39

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
ggcatcgggt tgctacccaa ggacaagagt cgatgcc 37

<210> SEQ ID NO 64
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64
cgucaucggg uugcuaccca aggucaggug acgaugacg 39

<210> SEQ ID NO 65
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 65
cgucaucggg uugcuaccca aggucaggag acgaugacg 39

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
tcgtcgtttt gtcgttttgt cgtt 24

<210> SEQ ID NO 67
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 67
tcgtcgtttt gtcgttttgt cgtt 24

<210> SEQ ID NO 68
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
tcgtcgtttt gtcgttttgt cgttcgucau cggguugcua cccaaggcca ggaggcgaug 60
acg 63

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cggguugcua cccaag 16

<210> SEQ ID NO 70
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aagccauuac cggguugcua cccaaggaca agagucgaug augcuu 46

<210> SEQ ID NO 71
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aagcauuacc ggguugcuac ccaaggacaa gagucgauga ugcuu 45

<210> SEQ ID NO 72
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aagccauuac cggguugcua cccgaggaca agagucgaug augcuu 46

<210> SEQ ID NO 73

<211> LENGTH: 46
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 73
aagccauuau cggguugcua cccaaggaca agagucgaug augcuu 46

<210> SEQ ID NO 74
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 74
cauuaucggg uugcuaccca aggacaagag ucgaugaug 39

<210> SEQ ID NO 75
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 75
cauuaucggg uugcuacccg aggacaagag ucgaugaug 39

<210> SEQ ID NO 76
<211> LENGTH: 54
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 76
gacuagaucg gguugcuacc caagcuccgg uucagaucga uggaggaucu aguc 54

<210> SEQ ID NO 77
<211> LENGTH: 41
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 77
cgucaucggg uugcuaccca aggcccagga gggcgaugac g 41

<210> SEQ ID NO 78
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 78
cgucaucggg uugcuaccca aggcaccagg aggugcgaug acg 43

<210> SEQ ID NO 79
<211> LENGTH: 39

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79

cgggaguccu aggaaggacg gguugcuacc caagucccg                           39


<210> SEQ ID NO 80
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80

gacuagaucg gguugcuacc caagcucccgg uucagaucga uggaggaucu aguc          54


<210> SEQ ID NO 81
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81

cgucaucggg uugcuaccca aggcccagga gggcgaugac g                        41


<210> SEQ ID NO 82
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82

cgucaucggg uugcuaccca aggcaccagg aggugcgaug acg                      43


<210> SEQ ID NO 83
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83

cgggaguccu aggaaggacg gguugcuacc caagucccg                           39
```

GPC3-BINDING APTAMER CHIMERA AND METHOD OF USE THEREOF TO STIMULATE AN IMMUNE RESPONSE IN A TUMOR TISSUE

CROSS REFERENCE TO RELATED APPLICATIONS

This application is a 35 U.S.C. § 371 National Stage Application of International Application No. PCT/US2021/059062, filed on Nov. 12, 2023, which claims the benefit of priority of U.S. Provisional Patent Application No. 63/113,640, filed on Nov. 13, 2020, entitled "GPC3 APTAMERS AND VARIANTS AND USE THEREOF", the contents of which are incorporated herein by reference in their entireties.

REFERENCE TO THE SEQUENCE LISTING

The present application is being filed along with a Sequence Listing in electronic format. The Sequence Listing is provided as a file entitled GBT_002US1_SL.txt, created on Dec. 11, 2023, which is 23,018 bytes in size. The information in the electronic format of the sequence listing is incorporated herein by reference in its entirety.

FIELD OF THE DISCLOSURE

The present disclosure relates to aptamers and variants thereof that specifically bind to glypican-3 (GPC3) protein. GPC3 aptamer conjugates and compositions thereof for cell-type specific targeting are also provided. The present GPC3 aptamers, aptamer conjugates and compositions can be used to induce activation of the immune system and/or for targeted cancer treatment.

BACKGROUND OF THE DISCLOSURE

Glypican-3 (GPC3) is a heparan sulfate (HS) proteoglycan highly expressed in the plasma membrane of most hepatocellular carcinoma (HCC) cells, but not in normal liver tissue or benign hepatocellular nodules (reviewed by Nishida and Kataoka, *Cancers,* 2019, 11(9): 1339). During early development, GPC3 is found in the fetal organs including, liver, lung, placenta, and kidney. GPC3 is absent or lowly expressed in most adult tissues (Iglesias et al., *Histol Histopathol.* 2008; 23:1113-40. 10.14670/HH-23.1333). GPC3 has been known to be involved in cell division and the control of cell division pattern during development. Studies have suggested that the GPC3 core protein may participate in binding Wnt as a co-receptor. GPC3 HS chains have also been shown to bind molecules including Wnt, HGF and Yap. By attracting and storing growth factors via HS chains and recognizing Wnt as a co-receptor, GPC3 acts as a cell surface glycoprotein that modulates Wnt signaling and pathways in liver cancer (e.g., Gao et al., *PLoS ONE.* 2015, 10:e0137664. 10.1371/journal.pone.0137664; and Li et al., *Hepatology.* 2019:30646 10.1002/hep.30646).

Liver cancer is the second leading cause of cancer related deaths worldwide, and hepatocellular carcinoma (HCC) is the most common type of primary liver cancer. Because only 40% of HCC patients are detected at an early stage (Reviewed by European Association for the Study of the Liver EASL clinical practice guidelines: Management of hepatocellular carcinoma. *J Hepatol.* 2018; 69(1):182-236), molecular targets for hepatocellular carcinoma early diagnosis and development of targeted therapy are critically needed for HCC with poor prognosis.

It has been shown that GPC3 is a promising target for HCC treatment, and a potential biomarker for diagnosis of HCC at early stage. Overexpression of GPC3 in HCC, OCCC (ovarian clear cell carcinoma), melanomas, lung squamous cell carcinomas, hepatoblastomas, nephroblastomas (Wilms' tumors), and yolk sac tumors, as well as in certain stomach cancers, for example, gastric cancers that produce α-fetoprotein, makes it an ideal target for cancer therapy. Recent studies have shown that GPC3 can act as an immunotherapeutic target in hepatocellular carcinoma. An array of strategies targeting GPC3 are currently in development and undergoing testing including cancer GPC3 peptide vaccines, antibody therapy, adoptive immunotherapy with TCR- or CAR-transduced T cells, and others.

Like other therapeutics, cancer immunotherapies can sometimes bind normal tissues, causing severe side effects. Targeted delivery of therapeutics could decrease such side effects. Aptamers possess many attractive features for targeted delivery of therapeutics including those therapeutics used in cancer immunotherapy. Aptamers have a smaller size (6-30 kDa, 2 nm) and flexible structure, allowing them to bind to smaller targets or hidden binding domains that are inaccessible for larger antibodies (150-180 Kda, 15 nm). The large size of antibodies may limit the tissue penetration of antibody-drug conjugates (ADCs), particularly in solid tumors, which may compromise their therapeutic efficacy. Furthermore, aptamers can be isolated within days via a cost-efficient in vitro selection procedure (e.g., SELEX), as compared to the lengthy, laborious and expensive in vivo screening process involved in antibody generation. Moreover, the propensity of aptamers to form complementary base pairs confers additional benefits, in that the function of aptamers can be modulated in vivo using complementary antidote oligonucleotides to disrupt aptamer function by base pairing with the active motifs of the aptamers.

Aptamers with specific affinity for GPC3 could serve as a targeting moiety to direct HCC treatments deep into the cancerous tissue. Moreover, aptamers specific to GPC3 can be used both as detection agents for early diagnosis, and as imaging probes for viewing HCC in vivo. The present disclosure identified a group of aptamers that share a common structural motif or a core nucleic acid sequence. The identified aptamers bind to GPC3 with high affinity and specificity. In accordance, the GPC aptamers disclosed herein can be conjugated to drugs such as cancer immunotherapeutics for targeted therapeutic delivery.

SUMMARY OF THE DISCLOSURE

In one aspect of the present disclosure, nucleic acid aptamers that specifically bind to GPC3 protein are provided. A GPC3 aptamer identified in the present disclosure comprises a core common nucleic acid sequence. The core common sequence comprises a nucleic acid of 5'CGZ$_3$GTTGCTACZ$_{12}$CRAG 3' (SEQ ID NO.: 7), wherein Z$_3$ and Z$_{12}$ form a base pair (i.e., AT or GC base pair), and R can be any nucleotide, A, T, G or C. In some embodiments, the GPC3 aptamer identified in the present disclosure comprises a conservative secondary structural including a bulge stem loop, followed by two stems with various length and sequences.

In some embodiments, the GPC3 aptamer identified in the present disclosure comprises a nucleic acid sequence selected from the group consisting of SEQ ID NOs.: 8-65 and 76-83. In some embodiments, a variant of the present GPC3 aptamer is provided. In other embodiments, the GPC3 aptamer variants have at least 60%, 70%, 80%, 85%, 86%, 87%, 88%, 89%, 90%, 91%, 92%, 93%, 94%, 95%, 96%, 97%, 98%, or 99% sequence identity to the nucleic acid sequence set forth in any of SEQ ID NOs.: 8-65 and 76-83.

Preferably the present GPC3 aptamer comprises a nucleic acid sequence presented by 5' CGUCAUCGGGUUGC-UACCCAAGGACAAGAGUCGAUGACG3' (SEQ ID NO.: 23), 5' CGUCAUCGGGUUGCUACCCAAGGU-CAAGAGACGAUGACG3' (SEQ ID NO.: 24), 5' CGU-CAUCGGGUUGCUACCCAAGGCCAG-GAGGCGAUGACG3' (SEQ ID NO.: 25), 5' GACUAGAUCGGGUUGCUACCCAAGCUCCG-GUUCAGAUCGAUGGAGGAUCUAG UC 3' (SEQ ID NO.: 76), 5' CGUCAUCGGGUUGCUACC-CAAGGCCCAGGAGGGCGAUGACG 3' (SEQ ID NO. 77), 5' CGUCAUCGGGUUGCUACCCAAGGCACCAG-GAGGUGCGAUGACG 3' (SEQ ID NO.: 78), or 5'CGG-GAGUCCUAGGAAGGACGGGUUGCUACCCAAGU-CCCG 3' (SEQ ID NO.: 79), or a variant thereof. For example, the GPC3 aptamer variant may comprise a nucleic acid sequence that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 23, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 24, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 25, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 76, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 77, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 78, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 79. In some embodiments, the GPC3 aptamer variant may comprises at least 15-21 consecutive nucleotides of the nucleic acid sequence selected from the group consisting of SEQ ID NOs.: 8-65 and 76-83.

The GPC3 aptamer of the present disclosure may be modified at the 5' end, 3' end, both ends, and in the middle of the sequence. In some examples, one, two, three, four, five, six or more residues may be modified.

In some embodiments, the GPC3 aptamer comprises at least one modification, such as 2'OME. In other embodiments, the GPC3 aptamer comprises a nucleic acid sequence in which all the nucleotides are modified with 2'OME. As non-limiting examples, the GPC3 aptamer is selected from the group consisting of SEQ ID NOs.: 37-65. In one preferred embodiment, the GPC3 aptamer comprises a nucleic acid sequence selected from the group consisting of SEQ ID NOs.: 52-54 and 80-83.

In another aspect of the present disclosure, a GPC3 aptamer conjugate is provided. The GPC3 aptamer conjugates comprising a GPC3 aptamer and a therapeutic, which may be, but is not limited to, a therapeutic nucleic acid molecule, a compound, an antibody or variant thereof, a peptide, a protein, a toxin, a cell, or an immunotherapeutic agent.

In some embodiments, the GPC3 aptamer conjugate is an aptamer chimera comprising a GPC3 aptamer of the present disclosure, or a variant thereof, and a therapeutic nucleic acid molecule, including but not limited to a therapeutic aptamer, an oligonucleotide, an anti-sense oligonucleotide (ASO), a siRNA, a shRNA, a saRNA, an mRNA, a microRNA and a gene therapy.

In some embodiments, the GPC3 aptamer conjugate is an aptamer drug conjugate in which a GPC3 aptamer is covalently or non-covalently conjugated to a drug, such as a chemotherapeutic drug.

In some embodiments, the GPC3 aptamer conjugate is an aptamer-antibody conjugate in which a GPC3 aptamer is covalently or non-covalently conjugated to an antibody or a functional fragment or variant thereof.

In some embodiments, the GPC3 aptamer conjugate is an immunotherapeutic conjugate in which a GPC3 aptamer is covalently or non-covalently conjugated to an immunotherapeutic agent such as a cancer vaccine, a checkpoint inhibitor, and a cell.

In another aspect of the present disclosure, a GPC3 aptamer complex is provided, the GPC3 aptamer complex may comprise one or more GPC3 aptamers conjugated to a drug delivery vehicle such as a liposome, a nanoparticle, an exosome or the like. In some embodiments, the nanoparticle, liposome or exosome is loaded with a medicine such as a therapeutic nucleic acid molecule, a compound, an antibody or variant thereof, a peptide, a protein, a toxin, a cell, or an immunotherapeutic agent. In some examples, the GPC3 aptamer is attached covalently or non-covalently to the nanoparticle, liposome or exosome.

Another aspect of the present disclosure includes a composition comprising any of the aptamers, aptamer conjugates and aptamer complexes described herein. In some embodiments, the composition further comprises a pharmaceutically acceptable carrier.

GPC3 is a surface protein over-expressed in the cell membrane of a hepatocellular carcinoma (HCC) cell. The GPC3 aptamer of the present disclosure with specific and high binding activity may be used to label and/or image HCC cells for cancer diagnosis.

In another aspect of the present disclosure, a method of delivering a molecular entity to a GPC3 positive cell in a subject is provided. The delivery method comprises administering to the subject any of the compositions described herein, wherein the molecular entity is conjugated to the aptamer or contained in a liposome attached to the aptamer, so as to thereby deliver the molecular entity to the GPC3 positive cell. The molecular entity may be a therapeutic nucleic acid molecule, a compound, an antibody or variant thereof, a peptide, a protein, a toxin, a cell, or an immunotherapeutic agent.

The present disclosure provides a method of treating cancer in a subject comprising administering to the subject a therapeutically effective amount of a nucleic acid aptamer specific to GPC3, and/or any aptamer conjugates, complexes and compositions disclosed therein.

Additional aspects of the disclosure will be apparent from the description which follows.

DETAILED DESCRIPTION OF THE DISCLOSURE

Figure 1:
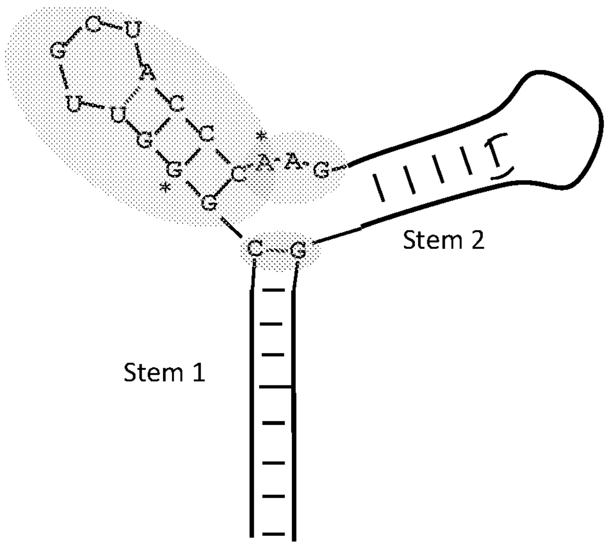
FIG. 1 is a representative GPC3 aptamer demonstrating the secondary structure and the common motif shared by GPC3 aptamers. Figure discloses SEQ ID NO.: 69.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

INTRODUCTION

The present disclosure identify a group of aptamers that specifically bind GPC3 protein. The GPC3 aptamers share a common core nucleic acid sequence and/or a common secondary structure. The present disclosure also discuss the GPC3 aptamer conjugates and use thereof for cancer diagnosis and treatment, particularly for GPC3 positive cancer, such as hepatocellular carcinoma (HCC), lung squamous cell carcinoma (SqCC), gastric carcinoma, ovarian carcinoma (such as ovarian clear cell carcinoma (OCCC)), melanomas, and pediatric embryonal tumors (e.g., Hepatoblastoma, nephroblastomas (Wilms' tumors) and yolk sac tumors).

DEFINITIONS

To more clearly and concisely describe the subject matter of the claimed disclosure, the following definitions are provided for specific terms, which are used in the following description and the appended claims. Throughout the specification, exemplification of specific terms should be considered as non-limiting examples.

As used herein, the terms "conjugated", or "conjugate" are used herein to refer to two or more entities that are linked by direct or indirect covalent or non-covalent interaction. In some embodiments, the interaction is covalent. In some embodiments, a covalent interaction is mediated by a linker moiety. In some embodiments, the interaction is non-covalent (e.g., charge interactions, affinity interactions, metal coordination, physical adsorption, host-guest interactions, hydrophobic interactions, stacking interactions, hydrogen bonding interactions such as with "sticky sequences," van der Waals interactions, magnetic interactions, electrostatic interactions, dipole-dipole interactions, etc.).

As used herein, the term "diagnose" refers to identify the nature of a medical condition of a subject, such as cancer, from its signs and symptoms.

As used herein, the term "pharmaceutical composition" refers to the combination of an active agent with a carrier, inert or active, making the composition especially suitable for diagnostic or therapeutic use in vivo or ex vivo. The carrier in the pharmaceutical composition must be acceptable in the sense that it is compatible with the active ingredient and capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

As used herein, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. In some examples, the compositions and formulations also can include stabilizers and preservatives.

As used herein, the term "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans, or generally recognized as safe for use in parenteral products.

As use herein, the terms "treating", or "treatment" refer to both therapeutic treatment and prophylactic or preventative measures. They refer to preventing, curing, reversing, attenuating, alleviating, minimizing, suppressing, or halting the deleterious effects of a disease state, disease progression, disease causative agent (e.g., bacteria or viruses), or other abnormal condition.

As used herein, the term "therapeutic agent" refers to an atom, molecule, or compound that is useful in the treatment of HCC, cancer or other conditions described herein. Examples of therapeutic agents that may be conjugated to a GPC3 aptamer include, but are not limited to, drugs, chemotherapeutic agents, immunotherapeutic agents, therapeutic antibodies and fragments thereof, toxins (e.g., immunotoxins), radioisotopes, enzymes (e.g., enzymes to cleave prodrugs to a cytotoxic agent at the site of the tumor), nucleases, hormones, immunomodulators, antisense oligonucleotides, nucleic acid molecules (e.g., mRNA molecules, cDNA molecules, microRNAs, saRNAs, or RNAi molecules such as siRNAs or shRNAs), chelators, boron compounds, photoactive agents and dyes. The therapeutic agent may also include a metal, metal alloy, intermetallic or core-shell nanoparticle bound to a chelator that acts as a radiosensitizer to render the targeted cells more sensitive to radiation therapy as compared to healthy cells.

As used herein, the term "therapeutically effective amount" generally refers to an amount of the aptamer of the present disclosure to affect a desired biological response. Such response may be a beneficial result, including, without limitation, amelioration, reduction, prevention, or elimination of symptoms of a disease or disorder. Therefore, the total amount of each active component of the aptamer or method is sufficient to demonstrate a meaningful benefit in a subject in need, including, but not limited to, treatment of cancer. A "therapeutically effective amount" may be administered through one or more preventative or therapeutic administrations. When a "therapeutically effective level" is applied to a single ingredient, administered alone, the term refers to that composition alone. When applied to a combination, the term refers to combined amounts of the active compositions that produce the therapeutic effect, whether administered in combination, consecutively, or simultaneously. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

As used herein, the terms "patient," "individual," or "subject" are used interchangeably and intended to include human and non-human animals. Exemplary human subjects include a human patient suffering from cancer, e.g., HCC. The term "non-human animals" includes all vertebrates, e.g., non-mammals (such as chickens, amphibians, reptiles) and mammals, such as non-human primates, domesticated and/or agriculturally useful animals (such as sheep, dogs, cats, rabbits, cows, pigs, etc.), and rodents (such as mice, rats, hamsters, guinea pigs, etc.

COMPOSITIONS OF THE PRESENT DISCLOSURE

The present disclosure relates to the isolation of unique aptamers that have clinical relevance for detection and diagnosis of GPC3 positive tumors such as hepatocellular carcinoma (HCC), lung squamous cell carcinoma (SqCC), gastric carcinoma, ovarian carcinoma (such as OCCC), melanomas, and pediatric embryonal tumors, in particular HCC. The GPC3 aptamers can also be used as targeting agents when conjugated to a drug to promote drug delivery specifically to GPC3 positive cancer cells. Provided in the present disclosure include GPC3 aptamers and variants thereof, aptamer conjugates and complexes, and pharmaceutical compositions comprising the GPC3 aptamers, aptamer conjugates and complexes, and the combination thereof.

GPC3

Glypican 3 (GPC3) is an oncofetal heparan sulfate (HS) glycoprotein attached to the surface of the cell membrane by a glycophosphatidylinositol (GPI) anchor. The GPC3 core protein consists of 580 amino acids. Two heparan sulfate side chains are attached near the C-terminal portion of the core protein. The single-chain GPC3 is processed by furin at the $Arg^{358}$-$Cys^{359}$ bond to generate the mature GPC3 consisting of a 40-kDa N-terminal subunit and a 30-kDa C-terminal subunit linked by disulfide bonds. The HS chain and core protein can bind to different factors and receptors for different functions.

GPC3 regulates cell proliferation signals by binding growth factors such as Wnt, fibroblast growth factor (FGF), and insulin-like growth factor (IGF) and plays an important role in the proliferation and differentiation of embryonic cells for morphogenesis and growth. GPC3 is expressed in various fetal tissues (liver, lung, kidney, and placenta) but is not detected in normal postnatal tissue due to DNA methylation-induced epigenetic silencing. However, GPC3 is abnormally overexpressed at cell surface in hepatocellular carcinoma (HCC), melanomas, ovarian clear cell carcinoma (OCCC) (Maeda et al., *Mod. Pathol.* 2009; 22:824-832. doi: 10.1038/modpathol.2009.40), gastric carcinoma (Ushiku et al., *Cancer Sci.* 2009; 100:626-632. doi: 10.1111/j.1349-7006.2009.01108.x), lung squamous cell carcinomas (Lin et al., *Med. Oncol.* 2012; 29:663-669. doi: 10.1007/s12032-011-9973-1), and pediatric embryonal tumors (e.g., hepatoblastomas, nephroblastomas, and ovarian yolk sac tumors) (Nakatsura et al., *Biochem Biophys Res Commun.* 2003; 306(1): 16-25; and Ortiz et al., *Front Oncol.* 2019; 9:108. doi: 10.3389/fonc.2019.00108). For example, GPC3 is detected in ≥80% of patients with HCC caused by hepatitis B or C. GPC3 is specifically expressed in liver cancer tissues and presents as soluble GPC3 (sGPC3) in peripheral blood of HCC patients, while its expression is not detected in the liver tissues of healthy adults, or pathological samples of fatty liver, or liver with cirrhosis, hepatitis, or injury, suggesting that GPC3 is a more reliable tumor marker. The level of GPC3 is associated with poor patient survival (reviewed by Zhou et al., *Medical Res. Rev.* 2017; 38(2):741-767).

GPC3 is suitable for targeted therapy as it is rarely expressed in other normal tissues of adults. The functional study of GPC3 in tumor progression has demonstrated that GPC3 may be a crucial molecule in cancer cell biology, and the cell surface GPI-anchored GPC3 might serve as a reservoir and cofactor for paracrine or autocrine growth factors to efficiently transduce activation signaling. Targeting GPC3 to regulate GPC3 activity, for example, shedding GPC3 from the cell surface, therefore, disturbing the pro-cancer signaling pathway, is a promising strategy for cancer treatment. Among the mechanisms of GPC3 targeting therapy, several therapeutics are under clinical trials for HCC and embryonic solid tumors and other cancers, such as GPC3 targeted antibody therapy, GPC3 peptide vaccine therapy and CAR-T immunotherapy.

Because of the overexpression pattern of GPC3 in most tumor cells, GPC3 is a promising target for targeted therapy of cancer. For example, anti-GPC3 antibodies have been studied for antibody-drug conjugates to specifically deliver cancer therapeutics to GPC3 positive tumor cells, guided by anti-GPC3 antibodies.

Aptamers

An aptamer is a biomolecule that binds to a specific target molecule and often modulates the target's activity, structure, or function. Aptamers often are referred to as "chemical antibodies," having similar characteristics as antibodies. An aptamer can be nucleic acid or amino acid based, i.e., either a nucleic acid aptamer or peptide aptamer. Nucleic acid aptamers have specific binding affinity to target molecules through interactions other than classic Watson-Crick base pairing. Nucleic acid aptamers are capable of specifically binding to selected targets with high affinity. Some aptamers through binding, can interfere their targets' ability to function. Aptamers of the present disclosure are synthetic oligonucleotides. A typical nucleic acid aptamer is approximately 10-15 kDa in size, binds its target with nanomolar to sub-nanomolar affinity, and discriminates against closely related targets. A target of a nucleic acid aptamer may be but is not limited to, a protein, a nucleic acid molecule, a peptide, a small molecule and a whole cell.

Nucleic acid aptamers may be ribonucleic acid (RNA), deoxyribonucleic acid (DNA), or mixed ribonucleic acid and deoxyribonucleic acid (DNA/RNA hybrid). Aptamers may be single stranded. A suitable nucleotide length for an aptamer ranges from about 15 to about 150 nucleotides, and in various other preferred embodiments, 15-30, 20-25, 20-35, 20-45, 20-50, 20-70, 25-35, 25-45, 25-50, 25-60, 25-70, 30-45, 30-50, 30-60, 40-60, 40-70, 50-80, 50-100, 70-120, any of 22, 23, 24, 25, 26, 27, 28, 29, 30, 31, 32, 33, 34, 35, 36, 37, 38, 39, or 40 nucleotides, in length. In some embodiments, an aptamer may be 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 nucleotides in length. In other embodiments, an aptamer may be 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 130, 140, or 150 nucleotides in length. However, the sequence can be designed with sufficient flexibility such that it can accommodate interactions of aptamers with targets.

As used herein, the terms "nucleic acid," "polynucleotide," "oligonucleotide" are used interchangeably. A nucleic acid molecule is a polymer of nucleotides consisting of at least two nucleotides covalently linked together. A nucleic acid molecule is a DNA (deoxyribonucleotide), an RNA (ribonucleotide), as well as a recombinant RNA and DNA molecule or an analogue of DNA or RNA generated using nucleotide analogues. The nucleic acids may be single stranded or double stranded, linear or circular. The term also comprises fragments of nucleic acids, such as naturally occurring RNA or DNA which may be recovered using the extraction methods disclosed, or artificial DNA or RNA molecules that are artificially synthesized in vitro (i.e., synthetic polynucleotides). Molecular weights of nucleic acids are also not limited, may be optional in a range from several base pairs (bp) to several hundred base pairs, for example from about 2 nucleotides to about 1,0000 nucleotides, or from about 10 nucleotides to 5,000 nucleotides, or from about 10 nucleotides to about 1,000 nucleotides.

The term "nucleotide (nt)" refers to the monomer of nucleic acids, a chemical compound comprised of a heterocyclic base, a sugar and one or more phosphate groups. The base is a derivative of purine and pyrimidine and the sugar is a pentose, either deoxyribose or ribose.

As used herein, the term "modification" refers to the technique of chemically reacting a nucleic acid, e.g., an oligonucleotide, with chemical reagents. A nucleic acid may be modified in the base moiety, sugar moiety or phosphate backbone. The modifications include, but are not limited to, 2'-position sugar modifications, 5-position pyrimidine, modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping. The nucleic acid molecule may also be modified by conjugation to a moiety having desired biological properties. Such moiety may include, but is not limited to, compounds, peptides and proteins, carbohydrates, antibodies, enzymes, polymers, drugs and fluorophores. In some examples, the polynucleotide is conjugated to a lipophilic compound such as cholesterol, dialkyl glycerol, diacyl glycerol, or a non-immunogenic, high molecular weight compound or polymer such as PEG (polyethylene glycol) or other water soluble pharmaceutically acceptable polymers including, but not limited to, polyaminoamines (PAMAM) and polysaccharides such as dextran, or polyoxazolines (POZ). The modifications may be intended, for example, to increase the in vivo stability of nucleic acid molecules or to enhance or to mediate delivery of the molecules.

Aptamers may be either monovalent or multivalent. Aptamers may be monomeric, dimeric, trimeric, tetrameric or other higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holliday junction-like) DNA nanostructure will be engineered to include sequences complementary to the 3'-arm regions of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors. Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sites or a multimeric aptamer that binds to different target molecules. A heteromultimer that binds to different target molecules can also be referred to as a multispecific multimer.

Nucleic acid aptamers comprise a series of linked nucleosides or nucleotides. The term "nucleic acid," in its broadest sense, includes any compound and/or substance that comprise a polymer of nucleotides. These polymers are often referred to as polynucleotides. Exemplary nucleic acid molecules or polynucleotides of the invention include, but are not limited to, either D- or L-nucleic acids, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid.

Aptamers can be generated against a target molecule (e.g., GPC3) using a process called either in vitro selection (Ellington and Szostak; In vitro selection of RNA molecules that bind specific ligands. Nature. 1990; 346:818-822) or SELEX (Tuerk and Gold, Systematic evolution of ligands by exponential enrichment: RNA ligands to bacteriophage T4 DNA polymerase; Science, 1990, 249:505-510). This method allows the in vitro evolution of nucleic acid molecules with highly specific binding to target molecules. The SELEX method is described in, for example, U.S. Pat. Nos. 7,087,735, 5,475,096 and 5,270,163; the contents of each of which are incorporated herein by reference in their entirety. Nucleic acid aptamers can be synthesized using methods well-known in the art. For example, the disclosed aptamers may be synthesized using standard oligonucleotide synthesis technology known in the art.

In some embodiments, the aptamer comprises at least one chemical modification. In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG). The process of covalent conjugation of PEG to another molecule, normally a drug or therapeutic protein is known as PEGylation. PEGylation is routinely achieved by incubation of a reactive derivative of PEG with the target molecule. The covalent attachment of PEG to a drug or therapeutic protein can mask the agent from the host's immune system, thereby providing reduced immunogenicity and antigenicity, and increase the hydrodynamic size (size in solution) of the agent which prolongs its circulatory time by reducing renal clearance. PEGylation can also provide water solubility to hydrophobic drugs and proteins.

In some embodiments, nucleic acid aptamers are provided in which the P(O)O group is replaced by P(O)S ("thioate"), P(S)S ("dithioate"), P(O)NR2 ("amidate"), P(O)R, P(O)OR', CO or CH2 ("formacetal") or 3'-amine (—NH—CH2-CH2-), wherein each R or R' is independently H or substituted or unsubstituted alkyl. Linkage groups can be attached to adjacent nucleotide through an —O—, —N—, or —S— linkage. Not all linkages in the nucleic acid aptamers are required to be identical.

As non-limiting examples, a nucleic acid aptamer can include D-ribose or L-ribose nucleic acid residues and can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, an inverted deoxynucleoside or inverted ribonucleoside, a 2'-deoxy-2'-fluoro-modified nucleoside, a 2'-amino-modified nucleoside, a 2'-alkyl-modified nucleoside, a morpholino nucleoside, a phosphoramidate or a non-natural base comprising nucleoside, or any combination thereof. Alternatively, a nucleic acid aptamer can comprise at least two modified ribonucleosides, at least 3, at least 4, at least 5, at least 6, at least 7, at least 8, at least 9, at least 10, at least 15, at least 20 or more modified ribonucleosides, up to the entire length of the molecule. The modifications need not be the same for each of such a plurality of modified deoxy- or ribonucleosides in a nucleic acid molecule.

An aptamer of the present invention may include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, those disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993.

In some embodiments, the nucleic acid aptamer comprises one or more regions of double-stranded character. Such double stranded regions may arise from internal self-complementarity or complementarity with a second or further aptamers or oligonucleotide molecule. In some embodiments, the double stranded region may be from 4-12, 4-10, 4-8 base pairs in length. In some embodiments, the double stranded region may be 5, 6, 7, 8, 9, 10, 11 or 12 base pairs. In some embodiments, the double stranded region may form a stem region. Such extended stem regions having double stranded character can serve to stabilize the nucleic acid aptamer. As used herein, the term "double stranded character" means that over any length of two nucleic acid molecules, their sequences form base pairings (standard or nonstandard) of more than 50 percent of the length.

Aptamers may be further modified to provide protection from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamers. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants. The resistance of these modified aptamers to nuclease can be tested by incubating them with either purified nucleases or nuclease from mouse serum, and the integrity of aptamers can be analyzed by gel electrophoresis.

In some embodiments, such modified nucleic acid aptamers may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modifications. For example, all purine nucleotides may have one type of modification (or are unmodified), while all pyrimidine nucleotides have another, different type of modification (or are unmodified). In this way, oligonucleotides, or libraries of oligonucleotides are generated using any combination of modifications as disclosed herein.

According to certain embodiments of the present invention, variants and derivatives of aptamers are provided. The term "derivative" is used synonymously with the term "variant" and refers to a molecule that has been modified or changed in any way relative to a reference or starting aptamer. The nucleic acid sequence of aptamer variants may possess substitutions, deletions, and/or insertions at certain positions within the nucleotide sequence, as compared to a reference or starting sequence. Ordinarily, variants will possess at least about 50% identity (homology) to a reference sequence, and preferably, they will be at least about 80%, more preferably at least about 90% identical (homologous) to a reference sequence.

In some embodiments, variant mimics of aptamers of the present disclosure are provided. As used herein, the term "variant mimic" is one which contains one or more nucleic acids which would mimic an activated sequence. The nucleic acid sequences of variant mimics may comprise naturally occurring nucleic acids, or alternatively, non-naturally occurring nucleic acids.

An aptamer may be labeled with a fluorescent marker which generates detectable fluorescent signals. As non-limiting examples, the fluorophore may be selected from, Alex Fluor® fluorophores (such as Alex 514, Alex 532, Alex 546, Alex 555, Alex 568, Alex 594, Alex 610, Alex 633, Alex 635, Alex 647, Alex 660, Alex 680, Alexa 700, Alex 750, Alex 800, Alex 610-R-phycoerythrin (R-PE), Alex 647-R-phycoerythrin (R-PE), Alex 680-R-phycoerythrin (R-PE), and Alex 680-Allophycocyanin (APC)), Allophycocyanin (APC) and its derivatives, Cy fluorophores (e.g., Cy3.5, Cy3-FITC, CY5, CY 5.5, CY7, CY7-APC, CY5.5-APC), Qdots, TRITC, R-PE, Tamara, Rhodamine Red-X, Rox, TruRed, SYPRO red, BODIPY TR, Propidium iodide and Texas red. In some examples, the fluorophore is Alex 647, Cy5, CY3-FITC or Texas red.

GPC3 Aptamers and Variants

The present disclosure provides a group of aptamers that can specifically bind to GPC3 with high affinity.

Aptamers that specifically bind to GPC3 protein were screened and identified. Characterization of aptamers isolated by SELEX screening identifies a core-binding sequence present in all positive clones. The common core nucleic acid sequence comprises a sequence of 5' $CGZ_3GTTGCTACZ_{12}CRAG$-3' (SEQ ID NO. 7), wherein Z at positions 3 and 12 form base pair (e.g., $Z_3$ is G/C and $Z_{12}$ is C/G; or $Z_3$ is A/T and $Z_{12}$ is T/A) and wherein R can be any nucleotide, A, T, G or C. The core nucleic acid sequence is confined to a relatively simple structural motif in the form of a stem loop. FIG. 1 depicts the structural arrange conserved in all the GPC3 aptamers. The conserved structural motif comprises a loop structure that consistently links two stems (Stem 1 and Stem 2) with various lengths. The sequences of the double stranded stems 1 and 2 vary from each other. The sizes of stems 1 and 2 can be variable. The double-stranded stem 1 and stem 2 may have any number of base pairs provided the base pairing is stable under suitable binding buffer conditions, e.g., 4 base pairs to 10 base pairs, or 5 base pairs to 8 base pairs, or 4 base pairs, 5 base pairs, 6 base pairs, 7 base pairs, 8 base pairs, 9 base pairs or 10 base pairs. In addition, stems 1 and 2 may end in a loop, or the loop may be absent. As shown in FIG. 1, Stem 2 ends in a loop while stem 1 has no loop at the end. The loops of stem 1 and 2 can be variable in sequence and/or size or deleted entirely.

TABLE 1

Sequences of GPC3 aptamers

| | SEQUENCE (5'-3') | SEQ ID NO. |
|---|---|---|
| Common core sequence | $CGZ_3GTTGCTACZ_{12}CRAG$ ($Z_3$ is A/T and $Z_{12}$ is T/A; or $Z_3$ is G/C and $Z_{12}$ is C/G; R is A, T, G, or C) | 7 |
| GRX8 | CGUCAUCGGGUUGCUACCCAAGGACAAGAGUCGAUG ACG | 23 |
| GRX46 | CGUCAUCGGGUUGCUACCCAAGGUCAAGAGACGAUG ACG | 24 |
| GRX49 | CGUCAUCGGGUUGCUACCCAAGGCCAGGAGGCGAUG ACG | 25 |
| GRX958 | GACUAGAUCGGGUUGCUACCCAAGCUCCGGUUCAGA UCGAUGGAGGAUCUAGUC | 76 |
| GRX1187 | CGUCAUCGGGUUGCUACCCAAGGCCCAGGAGGGCGA UGACG | 77 |
| GRX2101 | CGUCAUCGGGUUGCUACCCAAGGCACCAGGAGGUGC GAUGACG | 78 |
| GRX2102 | CGGGAGUCCUAGGAAGGACGGGUUGCUACCCAAGUC CCG | 79 |

In some embodiments, the GPC3 aptamer may be further modified at the 5' end, 3' end, both ends, and/or in the middle. The modification of aptamer can be performed by combining one or more modifications, including but not limited to, PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol, etc. to the 5' end, 3' end, both ends, and/or the middle of the GPC3 aptamer.

The GPC3 aptamer of the present disclosure may be further modified with 5' and/or 3' caps. In some embodiments, the GPC3 aptamer is modified with idT (inverted deoxythymidine). Capping the 3'-end with idT (inverted deoxythymidine) is generally used to prevent decomposition of an aptamer by 3' exonuclease in human serum (Shum et al., *Chem biochem.* 2008; 9:3037-3045. doi: 10.1002/cbic.200800491). The present GPC3 aptamer may be modified with 3' biotin. Alternatively, the GPC3 aptamer may be modified at the 5' end, such as modifications with hydrophobic and/or bulky moiety, e.g., Cholesterol and diacylglycerol (DAG) lipid anchor. While not wishing to be bound by any particular theory, these modifications may increase the half-life of the GPC3 aptamers in circulation.

In some embodiments, the GPC3 aptamer is PEGylated at the 5' end and/or the 3' end. PEG is non-toxic and nonimmunogenic and is approved by the Food and Drug Administration (FDA). The conjugation of polyethylene glycol (PEG) to aptamers can increase the residence time of the aptamer in the body and decrease degradation by metabolic enzymes.

In some embodiments, the GPC3 aptamer contains 2'-O-methyl (2'OME) nucleotides. As a non-limiting example, the GPC3 aptamer of the present disclosure is fully 2'O Methylated.

Other modification of the GPC3 aptamer may include deoxyuridine (dU) having a hydrophobic functional group substituted at 5-position of a pyrimidine group and phosphorothioate modification.

In some embodiments, the GPC3 aptamer or a salt thereof comprises a nucleic acid sequence selected from the group consisting of SEQ ID NOs.: 8-65 and 76-83. In one embodiment, the GPC3 aptamer may be a synthetic polynucleotide comprising at least 15-21 consecutive nucleotides of any one of the sequences of SEQ ID NOs.: 8-65 and 76-83. Additionally, the synthetic sequence may comprise a stem-loop structure.

In other embodiments, the GPC3 aptamer comprises a nucleic acid sequence having at least 60%, 70%, 80%, 85%, 86%, 87%, 88%, 89%, 90%, 91%, 92%, 93%, 94%, 95%, 96%, 97%, 98%, or 99% sequence identity to the nucleotide sequence set forth in any of SEQ ID NOs.: 8-65 and SEQ ID NOs.: 76-83.

In some embodiments, the GPC3 aptamer comprises a nucleic acid sequence presented by 5' CGUCAUCGGGUUGCUACCCAAGGACAAGAGUCGAUGACG3' (SEQ ID NO.: 23), 5' CGUCAUCGGGUUGCUACCCAAGGUCAAGAGACGAUGACG3' (SEQ ID NO.: 24), 5' CGUCAUCGGGUUGCUACCCAAGGCCAGGAGGCGAUGACG3' (SEQ ID NO.: 25), 5' GACUAGAUCGGGUUGCUACCCAAGCUCCGGUUCAGAUCGAUGGAGGAUCUAG UC 3' (SEQ ID NO.: 76), 5' CGUCAUCGGGUUGCUACCCAAGGCCCAGGAGGGCGAUGACG 3' (SEQ ID NO. 77), 5' CGUCAUCGGGUUGCUACCCAAGGCACCAGGAGGUGCGAUGACG 3' (SEQ ID NO.: 78), or 5'CGGGAGUCCUAGGAAGGACGGGUUGCUACCCAAGUCCCG 3' (SEQ ID NO.: 79), or a variant thereof. For example, the GPC3 aptamer variant may comprise a nucleic acid sequence that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 23, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 24, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 25, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 76, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 77, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 78, or that is 60%, 70%, 80%, 85%, 86%, 87%, 88%, 89%, 90%, 91%, 92%, 93%, 94%, 95%, 96%, 97%, 98%, or 99% identical to the sequence presented by SEQ ID NO.: 79.

In some examples, the GPC3 aptamer comprises a nucleic acid sequence having at least 90% identity with any one of SEQ ID NOs: 8-65 and SEQ ID NOs.: 76-83. In some embodiments, the GPC3 aptamer comprises a nucleic acid sequence having at least about 15-21 consecutive nucleotides of a nucleic acid sequence having at least 90% identity with any one of SEQ ID NOs: 8-65 and SEQ ID NOs.: 76-83.

In some embodiments, the GPC3 aptamer contains 2'OME modification. In one embodiment, the GPC3 aptamer may comprise a nucleic acid sequence: 5' mCmGmUmCmAmUmCmGmGmGmUmUmGmCmUmAmCmCmCmAmAmGmGmAmC mAmAmGmAmGmUmCmGmAmUmGmAmCmG3' (SEQ ID NO.: 52). In another embodiment, the GPC3 aptamer may comprise a nucleic acid sequence: 5' mCmGmUmCmAmUmCmGmGmGmUmUmGmCmUmAmCmCmCmAmAmGmGmUmC mAmAmGmAmGmAmCmGmAmUmGmAmCmG 3' (SEQ ID NO.: 53). In another embodiment, the GPC3 aptamer may comprise a nucleic acid sequence: 5'mCmGmUmCmAmUmCmGmGmGmUmUmGmCmUmAmCmCmCmAmAmGmGmCm CmAmGmGmAmGmGmCmGmAmUmGmAmCmG 3' (SEQ ID NO.: 54). In another embodiment, the GPC3 aptamer may comprise a nucleic acid sequence: 5' mGmAmCmUmAmGmAmUmCmGmGmGmUmUmGmCmUmAmCmCmCmAmAmGmC mUmCmCmGmGmUmUmCmAmGmAmUmCmGmAmUmGmGmAmGmGmAmUmCmU mAmGmUmC3' (SEQ ID NO.: 80). In further another embodiment, the GPC3 aptamer may comprise a nucleic acid sequence: 5' mCmGmUmCmAmUmCmGmGmGmUmUmGmCmUmAmCmCmCmAmAmGmGmCmC mCmAmGmGmAmGmGmGmCmGmAmUmGmAmCmG3' (SEQ ID NO.: 81). In further another embodiment, the GPC3 aptamer may comprise a nucleic acid sequence: 5' mCmGmUmCmAmUmCmGmGmGmUmUmGmCmUmAmCmCmCmAmAmGmGmCmA mCmCmAmGmGmAmGmGmUmGmCmGmAmUmGmAmCmG3' (SEQ ID NO.: 82). In further another embodiment, the GPC3 aptamer may comprise a nucleic acid sequence: 5' mCmGmGmGmAmGmUmCmCmUmAmGmGmAmAmGmGmAmCmGmGmGmUmUmG mCmUmAmCmCmCmAmAmGmUmCmCmCmG3' (SEQ ID NO.: 83).

In other embodiments, the GPC3 aptamer may comprise a nucleic acid sequence selected from SEQ ID NO. 37-51, with 2'OME modification (Table 2).

TABLE 2 sequences of the selected GPC3 aptamers with 2'OME modifications

| SEQUENCE (5'-3') | SEQ ID NO. |
|---|---|
| mGmGmGmAmGmAmCmAmAmGmAmAmTmAmAmAmGmCmGmAmGmTmTmGmCmTmAmCmTmCmAmAmGmGmCmAmCmGmTmCmGmTmGmTmGmCmGmCmTmGmAmTmTmCmAmAmGmAmGmTmCmGmAmTmGmAmTmGmCmTmTmAmGmCmTmAmG | 37 |

TABLE 2-continued sequences of the selected GPC3 aptamers with 2'OME modifications

| SEQUENCE (5'-3') | SEQ ID NO. |
|---|---|
| mGmGmGmAmGmAmCmAmAmGmAmAmTmAmAmAmGmCmGmAmGmTmTmTmCm<br>GmTmGmTmCmGmTmGmTmTmGmCmTmAmCmAmCmAmAmGmTmCmCmGmTmTm<br>AmCmCmAmAmGmAmGmTmCmGmAmTmGmAmTmGmCmTmTmAmGmCmTmAmG | 38 |
| mGmGmGmAmGmAmCmAmAmGmAmAmTmAmAmAmGmCmGmAmGmTmTmAmAm<br>CmGmGmGmTmTmGmCmTmAmCmCmCmAmAmGmTmCmTmTmGmCmAmAmTmTm<br>CmGmCmAmAmGmAmGmTmCmGmAmTmGmAmTmGmCmTmTmAmGmCmTmAmG | 39 |
| mGmGmGmAmGmAmCmAmAmGmAmAmTmAmAmAmGmCmGmAmGmTmTmGmCm<br>AmTmGmAmTmCmGmTmGmTmTmGmCmTmAmCmAmCmGmAmGmGmTmCmTmCm<br>AmTmTmAmAmGmAmGmTmCmGmAmTmGmAmTmGmCmTmTmAmGmCmTmAmG | 40 |
| mGmGmGmAmGmAmCmAmAmGmAmAmTmAmAmAmGmCmGmAmGmTmTmTmGm<br>AmAmGmCmCmAmTmTmAmCmCmGmGmGmTmTmGmCmTmAmCmCmCmAmAmGm<br>GmAmCmAmAmGmAmGmTmCmGmAmTmGmAmTmGmCmTmTmAmGmCmTmAmG | 41 |
| mGmGmGmAmGmAmCmAmAmGmAmAmTmAmAmAmGmCmGmAmGmTmTmGmTm<br>TmGmCmAmTmCmGmAmGmTmTmGmCmTmAmCmTmCmAmAmGmGmTmCmGmCm<br>GmTmCmAmAmGmAmGmTmCmGmAmTmGmAmTmGmCmTmTmAmGmCmTmAmG | 42 |
| mGmGmGmAmGmAmCmAmAmGmAmAmTmAmAmAmGmCmGmAmGmTmTmGmCm<br>CmTmGmTmTmGmCmAmTmCmGmTmGmTmTmGmCmTmAmCmAmCmAmAmGmAm<br>TmTmGmAmAmGmAmGmTmCmGmAmTmGmAmTmGmCmTmTmAmGmCmTmAmG | 43 |
| mGmGmGmAmGmAmCmAmAmGmAmAmTmAmAmAmGmCmGmAmGmTmTmCmAm<br>TmCmGmTmGmTmTmGmCmTmAmCmAmCmAmAmGmGmAmCmTmCmTmAmGmCm<br>AmCmCmAmAmGmAmGmTmCmGmAmTmGmAmTmGmCmTmTmAmGmCmTmAmG | 44 |
| mGmGmGmAmGmAmCmAmAmGmAmAmTmAmAmAmGmCmGmAmGmTmTmGmTm<br>TmGmAmCmGmGmGmTmTmGmCmTmAmCmCmCmGmAmGmTmCmTmTmGmCmAm<br>TmTmCmAmAmGmAmGmTmCmGmAmTmGmAmTmGmCmTmTmAmGmCmTmAmG | 45 |
| mGmGmGmAmGmTmCmCmTmAmCmGmTmAmCmAmGmTmCmTmAmGmAmTmCmG<br>mGmGmTmTmGmCmTmAmCmCmCmAmAmGmCmTmGmCmGmGmTmAmCmAmAm<br>AmTmCmGmAmTmGmCmAmGmGmAmTmCmTmAmGmCmTmAmTmCmGmAmT | 46 |
| mGmGmGmAmGmTmCmCmTmAmCmGmTmAmCmAmGmTmCmTmAmGmGmAmCm<br>GmAmGmTmTmGmCmTmAmCmCmCmAmAmGmTmCmCmCmGmCmGmTmTmTmGm<br>AmTmCmGmAmTmGmCmAmGmGmAmTmCmTmAmGmCmTmAmTmCmGmAmT | 47 |
| mGmGmGmAmGmTmCmCmTmAmCmGmTmAmCmAmGmTmCmTmAmGmAmTmCmG<br>mGmGmTmTmGmCmTmAmCmCmCmAmAmGmCmTmGmCmGmGmTmTmCmAmAmA<br>mTmCmGmAmTmGmCmAmGmGmAmTmCmTmAmGmCmTmAmTmCmGmAmT | 48 |
| mGmGmGmAmGmTmCmCmTmAmCmGmTmAmCmAmGmTmCmTmAmGmAmTmCmG<br>mGmGmTmTmGmCmTmAmCmCmCmAmAmGmCmTmGmCmGmGmTmTmCmAmCmA<br>mTmCmGmAmTmGmCmAmGmGmAmTmCmTmAmGmCmTmAmTmCmGmAmT | 49 |
| mGmGmGmAmGmTmCmCmTmAmCmGmTmAmCmAmGmTmCmTmAmGmAmTmCmG<br>mGmGmTmTmGmCmTmAmCmCmCmAmAmGmCmTmGmCmGmGmTmAmCmAmGm<br>AmTmCmGmAmTmGmCmAmGmGmAmTmCmTmAmGmCmTmAmTmCmGmAmT | 50 |
| mGmGmGmAmGmTmCmCmTmAmCmGmTmAmCmAmGmTmCmTmAmGmAmTmCmG<br>mGmGmTmTmGmCmTmAmCmCmCmAmAmGmCmTmGmCmGmGmTmTmCmAmGmA<br>mTmCmGmAmTmGmCmAmGmGmAmTmCmTmAmGmCmTmAmTmCmGmAmT | 51 |
| mAmAmGmCmCmAmTmTmAmCmCmGmGmGmTmTmGmCmTmAmCmCmCmAmAmG<br>mGmAmCmAmAmGmAmGmTmCmGmAmTmGmAmTmGmCmTmT | 55 |
| mAmAmGmCmAmTmTmAmCmCmGmGmGmTmTmGmCmTmAmCmCmCmAmAmGm<br>GmAmCmAmAmGmAmGmTmCmGmAmTmGmAmTmGmCmTmT | 56 |
| mAmAmGmCmCmAmTmTmAmCmCmGmGmGmTmTmGmCmTmAmCmCmCmGmAmG<br>mGmAmCmAmAmGmAmGmTmCmGmAmTmGmAmTmGmCmTmT | 57 |
| mAmAmGmCmCmAmTmTmAmTmCmGmGmGmTmTmGmCmTmAmCmCmCmAmAmG<br>mGmAmCmAmAmGmAmGmTmCmGmAmTmGmAmTmGmCmTmT | 58 |
| mCmAmTmTmAmTmCmGmGmGmTmTmGmCmTmAmCmCmCmAmAmGmGmAmCmA<br>mAmGmAmGmTmCmGmAmTmGmAmTmG | 59 |
| mCmAmTmTmAmTmCmGmGmGmTmTmGmCmTmAmCmCmCmGmAmGmGmAmCmA<br>mAmGmAmGmTmCmGmAmTmGmAmTmG | 60 |

TABLE 2-continued sequences of the selected GPC3 aptamers with 2'OME modifications

| SEQUENCE (5'-3') | SEQ ID NO. |
|---|---|
| mCmGmTmCmAmTmCmGmGmGmTmTmGmCmTmAmCmCmCmAmAmGmGmAmCmA mAmGmAmGmTmCmGmAmTmGmAmCmG | 61 |
| mCmGmTmCmGmTmCmGmGmGmTmTmGmCmTmAmCmCmCmAmAmGmGmAmCmA mAmGmAmGmTmCmGmAmCmGmAmCmG | 62 |
| mGmGmCmAmTmCmGmGmGmTmmTGmCmTmAmCmCmCmAmAmGmGmAmCmAm AmGmAmGmTmCmGmAmTmGmCmC | 63 |
| mCmGmUmCmAmUmCmGmGmGmUmUmGmCmUmAmCmCmCmAmAmGmGmUmCm AmGmGmUmGmAmCmGmAmUmGmAmCmG | 64 |
| mCmGmUmCmAmUmCmGmGmGmUmUmGmCmUmAmCmCmCmAmAmGmGmUmCm AmGmGmAmGmAmCmGmAmUmGmAmCmG | 65 |

In other embodiments, the GPC3 aptamer of the present disclosure may further comprise a fluorescent molecule, a toxin, biotin, or a control reagent.

GPC3 Aptamer Conjugates

The high specificity and affinity of the GPC3 aptamer to the GPC3 protein make it a useful ligand for drug delivery. In accordance with the present disclosure, a GPC3 aptamer may be conjugated to one or more therapeutic agents, forming a therapeutic aptamer conjugate, wherein the GPC3 aptamer specifically binds to GPC3 expressed on the cell surface. The therapeutic agent may be a biologic, a therapeutic nucleic acid molecule, a compound, a protein such as an antibody and its functional fragment, a lipid, a peptide, a toxin such as an immunotoxin, a complex, an immunotherapeutic agent, a drug delivery vehicle such as nanoparticles (e.g., lipid nanoparticles (LNPs)), a whole cell and the like. In accordance, the GPC3 aptamers described herein may be used as a cell-specific delivery vehicle to deliver a therapeutic or diagnostic payload to GPC3 expressing cells, e.g., HCC cells.

GPC3 Aptamer Chimera

In accordance with the present disclosure, the GPC3 aptamer may be used in conjugation with another nucleic acid sequence to form an aptamer chimera. the nucleic acid molecule may be another therapeutic DNA or RNA aptamer, an oligonucleotide such as an anti-sense oligonucleotide (ASO), a gene therapy, a small/short interfering RNA (siRNA), a short hairpin RNA (shRNA), a microRNA, a small active RNA (saRNA), a mRNA, and the like. The aptamer chimera may be used to selectively deliver the conjugated nucleic acid molecule to a target cell, e.g., GPC3 expressing HCC cells.

Aptamers have been widely explored to be conjugated with small interfering RNA (siRNA), short hairpin RNA (shRNA) and microRNA (microRNA) for targeted delivery of these therapeutics for RNAi-based gene therapy of diseases (Thiel et al., *Nucleic Acids Res.* 2012; 40:6319-6337). For example, McNamara I I et al. developed aptamer-siRNA chimeric RNAs for specific binding of target cancer cells and subsequent specific delivery of siRNA into target cells (*Nat Biotechnol.* 2006; 24 (8): 1005-1015).

Cell type targeted siRNA delivery may be used to suppress expression of target genes that are associated with conditions or diseases that are particular to a certain cell population, tissue or organ, by exploiting the RNA interference (RNAi) system. In accordance, the GPC3 aptamer of the present disclosure may be conjugated to a siRNA molecule for cell type specific delivery.

In some embodiments, the aptamer chimera may be further optimized, including but not limited to truncation of the aptamer in order to reduce the synthesis and treatment cost, modification with 2'-fluoropyrimidines to increase the biostability, systematic engineering of the aptamer chimera to enhance the processing efficiency by RNA-induced silencing complex (RISC) machinery and further increase the silencing activity and specificity, and modification of the conjugate with a PEG to increase the in vivo circulation half-life.

In some embodiments, the siRNA molecule may be a bifunctional siRNA molecule. A bifunctional siRNA molecule can contain two fully target-complimentary and functional antisense strands against two targets at the same time but are only partially complementary to each other. The bifunctional design allows inhibiting of two genes simultaneously and therefore, these siRNAs may decrease off-target effects compared to conventional siRNAs due to the lack of undesired activity of the sense strand. Moreover, the simultaneous delivery of two effective antisense strands indicates the reduction of effective concentration of the siRNA drug, resulting in less toxicity and lower production costs.

A chimera may comprise a GPC3 aptamer and a siRNA. The GPC3 aptamer-siRNA chimera is targeted to GPC3 positive cancer cells and introduced to the RNAi pathway. Delivery of siRNAs to specific cells via cell-surface receptors should provide a maximal therapeutic benefit, decrease the therapeutically effective amount of drug needed, and avoid non-specific silencing or toxicity in healthy cells.

In some embodiments, the present GPC3 aptamers may be used for targeted gene therapy, by selective delivery of nucleic acid gene therapeutics to GPC3 positive tissues and cells.

In some embodiments, an aptamer chimera of the present disclosure comprises a GPC3 aptamer conjugated with a microRNA.

In some embodiments, an aptamer chimera of the present disclosure comprises a GPC3 aptamer conjugated with a second therapeutic aptamer or a therapeutic oligonucleotide. As a non-limiting example, the therapeutic oligonucleotide is an immunostimulatory oligonucleotide, such as a CpG immunostimulatory oligonucleotide. CpG is a cytosine-phosphate-guanine (CpG) dideoxynucleotide motif. As used there, the term "motif" is a "pathogen-associated molecular pattern" that mimics bacterial DNA and stimulates innate immune cells, thereby activating immune cells so that they are primed to recognize and kill cancer cells. The unmethylated CpG motif can be recognized by TLR and induce immune response. As used herein, the term "CpG immunostimulatory oligonucleotide" refers to a single stranded synthetic oligonucleotide (ODN) with unmethylated CpG motif that replace the native DNA ligands of TLR receptors to activate innate immunity in a subject. The activity of synthetic agonistic ODNs is affected by the position and number of CpG motifs, the sequence flanking the CpG motif, and the secondary structure formed by the ODNs. The immunostimulatory ODNs show sequence-species specificity for the activation of TLR receptors.

In some embodiments. The CpG immunostimulatory oligonucleotide may include the sequences disclosed in U.S. Pat. Nos. 6,207,646; 6,239,116; 6,653,292; 6,214,806; 6,406,705; 7,662,949; 8,128,944; 8,153,141; 8,354,522; 8,55,2165; 8,580,268; 8,834,900; 9,205,143; 9,382,545; 9,453,059 and 10,260,071; the contents of each of which are incorporated herein by reference in their entirety.

The GPC3 aptamer-CpG ODN may be used to stimulate immune cells to the tumor issue, or to decreases the intra-tumoral ratio of B cells, and/or to increase the intra-tumoral ratio of macrophages, T, NKT, and DC cells.

In one preferred embodiment, the CpG oligonucleotide is CpG7909 (5' TCGTCGTTTTGTCGTTTTGTCGTT3'; SEQ ID NO.: 66). In another embodiment, the CpG 7909 oligonucleotide contains pS linkage, comprising the sequence of 5' dTsdCsdGsdTsdCsdGsdTsdTsdTsdTsdGsdTsdCsdGsdTsd TsdTsdTsdGsdTsdCsdGsdTsdT 3' (SEQ ID NO.: 67).

As a non-limiting example, an aptamer chimera of the present disclosure is GRX51 (5'dTsdCsdGsdTsdCsdGsdTsdTsdTsdTsdGsdTsdCsdGsd TsdTsdTsdTsdGsdTsdCsdGsdTsd TmCmGmUmCmA-mUmCmGmGmGmUmUmGmCmUmAmCmCmCmA-mAmGmGmCm CmAmGmGmAmGmGmCmGmA-mUmGmAmCmG3'; SEQ ID NO.: 68).

Aptamer-Antibody Conjugates

Immunotherapy based on the use of novel human monoclonal antibodies (mAbs) with antitumor or immunomodulatory activity is an increasingly important strategy for cancer management. For example, mAbs can be directed against tumor-associated antigens (TAA) overexpressed on the cell surface of tumor cells, to either inhibit their oncogenic function or to specifically deliver toxic compounds. Alternatively, mAbs can be used in cancer therapy to regulate specific T-cell responses, thus enhancing the protective role of the immune system against cancer. In accordance with the present disclosure, the GPC3 aptamers, as carriers for cell-targeted delivery of therapeutic secondary reagents, are conjugated with a mAb for cancer therapy. The GPC3 aptamer will deliver the conjugated therapeutic mAb to GPC3 positive tumor cells. If necessary, structural changes may be introduced into the GPC3 aptamer for conjugation with a therapeutic mAb. An aptamer may be conjugated to the constant region of the antibody, for example, through a free amino group attached at the 5' end, or 3'end of the aptamer sequence. In some embodiments, an additional linker or spacer may be introduced into the aptamer to facilitate the aptamer-antibody conjugate.

As used herein, the term "antibody" is used in the broadest sense and specifically includes (but is not limited to) whole antibodies, monoclonal antibodies, polyclonal antibodies, multispecific antibodies (e.g., bispecific antibodies formed from at least two intact antibodies), antibody fragments, diabodies, antibody variants, and antibody-derived binding domains that are part of or associated with other peptides. Antibodies are primarily amino acid based molecules but may also comprise one or more modifications (including, but not limited to the addition of sugar moieties, fluorescent moieties, chemical tags, etc.).

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein the term, "antibody fragment" refers to any portion of an intact antibody. In some embodiments, antibody fragments comprise antigen binding regions from intact antibodies. Examples of antibody fragments may include, but are not limited to Fab, Fab', $F(ab')_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Compounds and/or compositions of the present invention may comprise one or more of these fragments. For the purposes herein, an "antibody" may comprise a heavy and light variable domain as well as an Fc region.

As used herein, the term "Fv" refers to antibody fragments comprising complete antigen-recognition and antigen-binding sites. These regions consist of a dimer of one heavy chain and one light chain variable domain in tight, non-covalent association.

As used herein, the term "Single-chain Fv" or "scFv" refers to a fusion protein of $V_H$ and $V_L$ antibody domains, wherein these domains are linked together into a single polypeptide chain. In some embodiments, the Fv polypeptide linker enables the scFv to form the desired structure for antigen binding.

As used herein, the term "bispecific antibody" refers to an antibody capable of binding two different antigens. Such antibodies typically comprise regions from at least two different antibodies.

As used herein, the term "diabody" refers to a small antibody fragment with two antigen-binding sites.

As used herein, the term "antibody variant" refers to a biomolecule resembling an antibody in structure and/or function comprising some differences in their amino acid sequence, composition or structure as compared to a native antibody.

Aptamer-antibody conjugation can be used directly against the same target (e.g., GPC3) or for targeted delivery to drugs (e.g., anti-cancer drugs). In accordance with the present disclosure, a GPC3 aptamer may be conjugated to antibody or its functional fragment or variant thereof. In some examples, the aptamer and the antibody target the same target protein in a cell. In other examples, aptamer and the antibody target different target proteins in a cell. Conjugation of aptamer and the antibody specific to the same target protein may have a higher affinity than antibody and aptamer alone.

In some embodiments, the GPC3 aptamer may be conjugated with anti-GPC3 antibodies such as GC33. GC33 is a monoclonal antibody targeting the carboxyl terminal subunit of GPC3. In mouse ectopic and in situ GPC3-positive HCC xenograft models, GC33 can significantly inhibit tumor growth mainly through antibody-dependent cell-mediated cytotoxicity (ADCC) (Nakano et al., *Biochem Biophys Res Commun.* 2009; 378(2):279-284). The GPC3 antibodies may also include antibodies against secreted N-terminal peptide of GPC3 present in blood or C-terminal peptide of GPC3 disclosed in US Patent Application Publication NO.: 20090060907 (the contents of which are incorporated herein by reference in their entirety), and monoclonal antibodies against GPC3 by Zhang et al (*Mol. Med. Rep.* 2019; 19(5): 3889-3895; the contents of which are incorporated herein by reference in their entirety).

In some examples, the antibody may be a bispecific antibody, e.g., ERY974 targeting GPC3 and CD3. ERY974 has a killing effect on a variety of GPC3 high expression tumors and can convert "cold tumor" into a highly inflammatory state "hot tumor." In other examples, the antibody may be a scFv-Fc antibody, e.g., a scFv-Fc of YP7 antibody that targets the carboxyl terminal epitope of GPC3 (Zhang and Ho, *Sci Rep.* 2016:33878). Other anti-GPC3 antibodies may include a high-affinity antibody HN3 targeting full-length GPC3 which can inhibit the proliferation of GPC3-positive cells by arresting the cell cycle in G1, and has a significant inhibitory effect on the growth of HCC xenografts in nude mice (Feng et al., *Proc Natl Acad Sci USA.* 2013; 110 (12): E1083-1091) and HS20 that targets heparan sulfate chain of GPC3, which blocked Wnt/β-catenin signaling, and inhibited WNT3a-dependent cell proliferation and HCC xenografts growth by blocking the interaction between Wnt3a and its ligand (Gao et al., *Hepatology.* 2014; 60 (2): 576-587).

In some embodiments, the present aptamer can be conjugated with an antibody-drug conjugate (ADC). E.g., YP7-Duocarmycin SA or pyrrolobenzodiazepine dimer-hYP7-DC and hYP7-PC (Fu et al., *Hepatology.* 2019; 70 (2): 563-576).

Aptamer Drug Conjugates

The high specificity and selectivity of the aptamers to GPC3 make the conjugates suitable for targeted delivery of therapeutics to GPC3 positive tissues and cells. The general chemical and thermal stability and conformational reversibility of these aptamers enable versatile designs of aptamer-drug conjugates. The chemical stability, simplicity of chemical modification, and ready molecular engineering of aptamers also enable easy and programmable conjugation with many therapeutics, ranging from chemotherapeutics to phototherapeutics, toxins, gene therapeutics, and vaccines. In some embodiments, drugs are conjugated to aptamers via functional linkers that ensure the stability of conjugates and also allow conditional drug release in targeted tissues or cells such as cancerous tissues or cells.

In some embodiments, a GPC3 aptamer drug conjugate may comprise an anti-cancer drug such as a chemotherapeutic drug. Conventional chemotherapy is limited by adverse side effects in healthy tissues and low maximum tolerated dosage, due to the off-target effects of many chemotherapeutic drugs. The ability to deliver chemotherapeutic drugs selectively to target cancer tissues is promising to overcome these complications. Aptamers are amenable to coupling with a wide range of chemotherapeutic drugs, owing much to their chemical stability and the ability of current technologies to design and site-specifically modify aptamers with desired functional groups.

In accordance with the present invention, a drug (e.g., anti-cancer drug) is conjugated to the GPC3 aptamer to form an aptamer-drug conjugate. The aptamer drug conjugates for targeted therapy can increase therapeutic effects specifically in targeted tissues such as tumor tissues while reducing toxicity in healthy tissues. In these conjugates, the GPC3 aptamers specifically recognize cancer associated GPC3 biomarker and deliver conjugated drugs to GPC3 positive tissues and cells.

In some embodiments, the anti-GPC3 aptamer may be conjugated with multiple copies of drugs by site-specifical conjugations.

In some embodiments, the aptamer drug conjugate may further comprise a linker that links the GPC3 aptamer to a chemotherapeutic drug. As a non-limiting example, a photocleavable (PC) linker may be used.

In some embodiments, the GPC3 aptamer is covalently conjugated to a chemotherapeutic drug. In other embodiments, the GPC3 aptamer is non-covalently conjugated to a chemotherapeutic drug. The chemotherapeutic drug may include doxorubicin (Dox), one of the most commonly prescribed chemotherapeutics in cancer therapy, 5-fluorouracil (5-FU), Drug Maytansinoid (DM1), and sorafenib.

In some embodiments, the drug may be an immunotoxin. An immunotoxin is a pharmacologically active biological preparation constructed from an antibody or a molecular ligand having a specific targeting function coupled to a toxin protein. As a non-limiting example, pseudomonas exotoxin A (PE-A) is the most commonly used toxin fragment in immunotoxins and can cause cell death by inhibiting protein synthesis in cells. Exemplary immunotoxins derived from combination of PE-A and GPC3 antibodies include immunotoxins YP7-PE38 and HN3-PE38, both of which have good anti-tumor activity in vivo and in vitro, and can induce regression of GPC3 positive xenografts; HN3-mPE24 and PE38KDEL (Wang et al., *Onstage.* 2017; 8(20):32450-32460). The immunotoxins may be conjugated with a GPC3 aptamer of the present disclosure for targeted delivery.

The therapeutics may be multikinase inhibitors such as sorafenib, Lenvatinib (a multikinase inhibitor that effectively inhibits vascular endothelial growth factor receptors (VEGFR) 1-3, fibroblast growth factor (FGF) receptors 1-4, platelet-derived growth factor receptor a, and RET, and KIT), cabozantinib (a tyrosine kinase inhibitor of VEGFR 1-3, MET, and AXL), ramucirumab (a VEGFR 2 antagonist), sunitinib (a multi-kinase blocker that targets VEGFR and PDGFR), linifanib (a multi-kinase inhibitor targeting VEGFR and PDGFR along with other kinases), brivanib (a selective inhibitor of fibroblastic growth factor receptor and VEGFR), tivantinib (an oral MET receptor tyrosine kinase inhibitor), everolimus (an inhibitor of mTOR), and other drugs targeting MARK, VEGF, EGF, insulin-like growth factor receptor, hepatocyte growth factor/c-MET, PI3K/PTEN/Akt/mammalian target of rapamycin (mTOR) and Wnt/β-Catenin pathways.

In some embodiments, the present anti-GPC3 aptamer may be conjugated to a drug targeting to another HCC therapeutic targets, such as surface molecules highly expressed on HCC cells, e.g., asialoglycoprotein receptor (ASGP-R), transferrin receptor (TfR), AF20 antigen, somatostatin receptor (SSTR), lysosome-associated protein transmembrane 4β (LAPTM4B). As compared to GPC3, ASGP-R, TfR, AF20 antigen, SSTR and LAPTM4B are not specific to HCC cells. GPC3 is rarely expressed in adult and not expressed in pathological liver cells such as hepatitis, cirrhosis, and fatty liver. GPC3 aptamer can specifically deliver drugs to HCC cells.

In one preferred embodiment of the present disclosure, a GPC3 aptamer-DM1 conjugate (GRX54) is provided.

Cancer Immunotherapy

In another aspect of the present disclosure, a GPC3 aptamer may be conjugated with an immunotherapeutic agent. The immunotherapy agents may include, but are not limited to, immune checkpoint inhibitors, such as anti-programmed cell death protein-1 (PD-1), anti-PD-1 ligand (PD-L1), and anti-cytotoxic T lymphocyte-associated protein-4 (CTLA-4) antibodies, immunomodulators such as STING agonists, TLR agonists, immunostimulatory antibodies and immunostimulatory oligonucleotides (e.g., CpG ODNs), cancer vaccine and CAR-T/NK cells.

In some embodiments, the immunotherapeutic agent is an immunomodulator including but not limited to, a small molecule STING-activating immunomodulator (e.g., 5,6-dimethylxanthenone-4-acetic acid (DMXAA), diABZIs, CDNs), ICOS agonists, CD40L, B7, B7RP1, and anti-CD40, anti-CD38, anti-ICOS, and 4-IBB ligands.

In some embodiments, the immunotherapeutic agents may be an immune accelerator therapies such as cancer vaccine therapy and chimeric antigen receptor-T cell (CAR-T) therapy. As used herein, the term "chimeric antigen receptor (CAR)" refers to a cell surface fusion protein containing an antigen recognition fragment, an immune cell receptor activating molecule, and a costimulatory signal molecule assembled by genetic engineering; after transfecting immune cells (such as NK, T cells, etc.) to express chimeric antigen receptors on the surface, CAR can accurately identify and direct immune cells to kill tumor cells. Some exemplary GPC3 CAR-Ts include CAR-T based on GC33 antibody, GPC3/ASGR1 bispecific CAR-T, which can specifically kill $GPC3^+ASGR1^+$ HCC (Chen et al., *Cancer Immunol Immunother.* 2017; 66(4):475-489).

In some embodiments, the immunotherapeutic agents may be photoimmunotherapy agents. Photoimmunotherapy is a new antibody-based biologic agent that is specifically enriched in carcinoma nest after the near-infrared phthalocyanine dye IR700 coupling with a specific antibody or biomacromolecule, and cell death can be induced by irradiating the drug-bound target cells with near-infrared light (Mitsunaga et al., *Nat Med.* 2011; 17(12):1685-1691). Exemplary immunotoxins include but are not limited to IR700-YP7 and IR700-HN3, based on YP7 antibody and NH3, both of which can significantly inhibit tumor growth (Hanankao et al., *Mol Pharm.* 2015; 12(6):2151-2157).

GPC3 Aptamer Complexes

In another aspect, the GPC3 aptamers of the present disclosure may be used as a targeting moiety of a drug delivery vehicle, such as liposome, lipid nanoparticle, extracellular microvesicle, exosome and the like.

In some embodiments, the GPC3 aptamer may be conjugated to a nanoparticle or a liposome that is loaded with a therapeutic agent such as an anticancer drug (e.g., an immunotherapeutic agent).

In some embodiments, the present GPC3 aptamers may be conjugated to a nanoparticle. The term "nanoparticle" as used herein refers to a biopolymer used as a carrier for drug delivery or diagnostic applications. Examples of biopolymers that may be processed as nanoparticles include, but are not limited to, chemically modified polysaccharides, and in particular, dextran. Other polymers such as polyesters may be used to form nanoparticles. Polyesters include PLGA, polyanhydride, PCL, poly beta amino esters, or other safe, non-toxic polymers. The term "nanoparticle" also includes, but is not limited to, a nanotube, for example a BCN nanotube, boron nitride nanotube, carbon nanotube, DNA nanotube, gallium nitride nanotube, silicon nanotube, inorganic nanotube, membrane nanotube, or titania nanotubes.

The nanoparticles may be poly(lactic-co-glycolic-acid) (PLGA) nanoparticles, PLGA-poly(ethylene glycol) (PEG) nanoparticles. The aptamer-functionalized nanoparticles (e.g., PLGA-PEG nanoparticles) are capable of sustained drug release, immune evasion, and specific targeting. Particularly, the tumor-specific aptamers modified on nanocarriers enhanced the drug delivery efficiency and subsequently improved tumor therapy efficacy.

In certain embodiments, the aptamer-conjugated nanoparticle is loaded with a therapeutic agent. As used herein, the term "therapeutic agent" refers to a substance that is capable of producing a curative effect in a disease state. Examples of therapeutic agents include, but are not limited to, alkylating agents, antimetabolites, anti-tumor antibiotics, topoisomerase inhibitors, mitotic inhibitors hormone therapy, targeted therapeutics and immunotherapeutic. In some embodiments the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-trans-retinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid. In certain embodiments, the therapeutic agent (also referred to as a "chemotherapeutic agent") is paclitaxel or carboplatin.

Liposomes, another well-established drug delivery system in the clinic, can also be conjugated with the present GPC3 aptamers for improved targeting and hence improved drug delivery efficiency. Liposomes may include PEG-containing lipids, cationic lipid containing liposome, soy-DOTAP liposome, etc.

In some embodiments, the present GPC3 aptamer may be modified on the surfaces of drug-loaded nanoparticles or liposomes for selective delivery of the encapsulated drugs to GPC3 positive tissues and cells.

In some embodiments, the GPC3 aptamer conjugated nanoparticles may be used for cancer cell detection. In this detection assay, silica-coated magnetic and fluorophore-doped silica nanoparticles are conjugated to highly selective GPC3 aptamers to detect and extract GPC3 positive cells.

Pharmaceutical Compositions and Formulations

In another aspect of the present disclosure, pharmaceutical compositions and formulations including GPC3 aptamers, GPC3 aptamer conjugates, GPC3 aptamer-complexes and the combinations, are provided. The compositions further include at least one pharmaceutically acceptable carrier, diluent or excipient. The composition may be formulated for administration by parental administration or enteral administration, or other appropriate routes. Parental administration may be performed by injection, or by the insertion of an indwelling catheter, including but not limited to intravenous (IV), intramuscular (IM), subcutaneous (SC), epicutaneous injection, peridural injection, intracerebral (into the cerebrum) administration, intracerebroventricular (into the cerebral ventricles) administration, extra-amniotic administration, nasal administration, intra-arterial, intracardiac, intraosseous infusion (IO), intraperitoneal infusion or injection, transdermal diffusion, enteral and gastrointestinal routes, topical administration and oral routes.

USAGE, APPLICATIONS AND METHODS

Diagnosis

Only 40% of HCC patients are detected at an early stage. There is a critical need to develop an innovative detection system. GPC3 is highly expressed in more than 70% of HCC patients and therefore may be an ideal biomarker for in vivo HCC diagnosis and imaging. Aptamers with specific affinity to GPC3 positive HCC may be used as agents for HCC diagnosis and imaging. The aptamers of the present disclosure can be used in various methods to assess presence or the expression level of GPC3 in a biological sample (e.g., a tumor sample).

In various embodiments directed to diagnostics or prognostics, one or more GPC3 aptamers are configured in a ligand-target based assay. The method may comprise contacting one or more GPC3 aptamers with a biological sample to be tested and the signal from the binding of the aptamers and GPC3 protein is measured to assess the presence and level of GPC3 in the biological sample.

Techniques of detecting biomarkers or capturing sample components using the GPC3 aptamer include the use of a planar substrate such as an array (e.g., biochip or microarray), with molecules immobilized to the substrate as capture agents that facilitate the detection of GPC3. The array can be provided as part of a kit for assaying GPC3 expression in a sample. In some embodiments, a GPC3 aptamer or other useful binding agent may be linked directly or indirectly to a solid surface or substrate. The GPC3 aptamer or other useful binding agent can be conjugated to a detectable entity or label. Appropriate labels include without limitation a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles, fluorophores, quantum dots, or radioactive labels. Using conventional techniques, the aptamer can be directly or indirectly labeled.

In some embodiments, the biomarker detection assay can be any assay available such as bead-based assays, microfluidics and flow cytometry.

The biological sample includes any relevant biological sample that can be used for biomarker assessment, including without limitation sections of tissues such as biopsy or tissue removed during surgical or other procedures, bodily fluids, autopsy samples, frozen sections taken for histological purposes, and cell cultures. Such samples include blood and blood fractions or products (e.g., serum, buffy coat, plasma, platelets, red blood cells, and the like), sputum, malignant effusion, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc. The sample can comprise biological material that is a fresh frozen & formalin fixed paraffin embedded (FFPE) block, or formalin-fixed paraffin embedded block. More than one sample of more than one type can be used for each patient.

Accordingly, the present aptamers may be used as anti-GPC3 probes to diagnose HCC and other GPC3 positive cancers. GPC3 has a higher positive rate in lung squamous cell carcinoma but has a lower positive rate in lung adenocarcinoma. A higher positive rate of GPC3 expression in yolk sac tumors (YST), including all YSTs associated with mixed germ cell tumors, it is a key marker for distinguishing between YST and clear cell carcinoma of the ovary (CCC).

In some embodiments, the present GPC3 aptamers, and variants thereof, may be used to diagnose GPC3 positive hepatocellular carcinoma (HCC), lung squamous cell carcinoma (SqCC), gastric carcinoma, ovarian clear cell carcinoma (OCCC), melanomas, and pediatric embryonal tumors (e.g., Hepatoblastoma, nephroblastomas (Wilms' tumors) and yolk sac tumors).

Diseases and Treatments

Primary liver cancer is the sixth most common malignant neoplasm and the second most common cause of cancer-related death worldwide. Hepatocellular carcinoma (HCC) is the most common form of primary liver cancer and over 80% of patients with HCC have liver cirrhosis associated with hepatitis B and C viral infection, alcohol abuse, or non-alcoholic fatty liver disease. GPC3 is a promising target for potential treatment of HCC. In accordance with the present disclosure, the GPC3 aptamers and variants thereof, GPC3 aptamer conjugates, GPC3 aptamer complexes and pharmaceutical compositions thereof may be used for treating a hepatocellular carcinoma, preventing a hepatocellular carcinoma, or inhibiting hepatocellular carcinoma metastasis. These GPC3 aptamers and variants thereof, GPC3 aptamer conjugates, GPC3 aptamer complexes and pharmaceutical compositions may also be used for treating other GPC3 positive cancers.

Accordingly, the present GPC3 aptamer mediates targeted delivery of therapeutics to tumor tissues and cells, increasing treatment efficiency and reducing off-target effects as well.

In some embodiments, the GPC3 aptamers may be used to guide GPC3 peptides to tumor tissues as cancer vaccines (GPC3 peptides that can bind to human leukocyte antigen (HLA)-A24 or -A2 and induce GPC3 peptide-specific CTLs), or deliver antibody therapy, immunomodulator agents, adoptive immunotherapy with TCR- or CAR-transduced T cells or NK cells.

In some embodiments, the present GPC3 aptamers can be used to guide antibody therapy targeting GPC3. Anti-GPC3 antibody therapies may include GC33, a humanized monoclonal antibody against GPC3 that has been shown to induce antibody-dependent cell-mediated cytotoxicity against GPC3-positive HCC cell lines and elicit anti-tumor effects in patient-derived xenograft cancer models (Ishiguro et al., *Cancer Res.* 2008; 68(23):9832-9838). In other examples, the GPC3 aptamer may be conjugated with other therapeutic antibodies for cancer treatment, such as monoclonal therapeutic antibodies.

In some embodiments, the GPC3 aptamer conjugate comprising an immunotherapeutic agent of the present disclosure may be used to treat HCC. For example, the present GPC3 aptamer may be used to guide GPC-CAR-T therapy (GPC3-CAR therapy against GPC3-positive HCC).

One of the major challenges in treating hepatocellular carcinoma (HCC) with current immunotherapies is turning cold tumors into immunogenic ones. Unmethylated CpG oligodeoxynucleotides (ODNs) are known immune stimulators, however their use in combination therapy for cancer treatment is limited due to the requirement of intra tumoral injections to prevent systemic toxicity. The present disclosure has demonstrated that a GPC3 aptamer-CpG conjugate, GRX51, can deliver the immunostimulatory CpG 7909 to GPC3-expressing cancer cells in vivo. Systemic administration through intra peritoneal (i.p.) injection of GRX51 decreases Hep3B tumor volume in a Balb/c nude mouse xenograft model by ~30-50% depending on treatment schedule, while also increasing immune cell infiltration.

In addition, the GPC3 aptamers and variants thereof, GPC3 aptamer conjugates, GPC3 aptamer complexes and pharmaceutical compositions thereof may be used for treatment of other GPC3 positive tumors including melanomas, ovarian clear cell carcinoma (OCCC), gastric carcinoma, lung squamous cell carcinomas, and pediatric embryonal tumors (e.g., hepatoblastomas, nephroblastomas, and ovarian yolk sac tumors).

In another aspect of the disclosure, a method of delivering a therapeutic agent to a GPC3 positive cell in a subject in need is provided. The method comprises administering to the subject a GPC3 aptamer of the present disclosure, wherein the aptamer is conjugated to a therapeutic agent.

In some embodiments, the present disclosure provides a method of treating a cancer in a subject in need thereof comprising administering to a subject a therapeutically effective amount of an aptamer conjugate. The aptamer conjugate comprises a GPC3 aptamer of the present disclosure and a therapeutic agent such as an immunotherapeutic agent.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

EXAMPLES

The following examples are offered by way of illustration and not by way of limitation.

Example 1: Selection of Anti-GPC3 Aptamers

Two different fully 2'Omethyl (2'OME) RNA oligonucleotide libraries were created and used for GPC3 binding aptamer selection. One oligonucleotide library (Pool1) is consisted of randomized oligonucleotides (N30) flanked by a 5' primer and 3' primer sites (5'GGGA-GACAAGAATAAAGCGAGTT(N30)AAGAGTCGAT-GATGCTTAGCTAG3'; SEQ ID NO.: 1). The 5' and 3' primers to amplify this pool comprise the sequences of 5'TAATACGACTCACTATAGGGA-GACAAGAATAAAGCGAGTT3' (SEQ ID NO. 2) and 5'CTAGCTAAGCATCATCGACTCTT3' (SEQ ID NO.: 3) respectively. A second oligonucleotide library (Pool8) consisting of randomized oligonucleotides (N30) flanked by a 5' primer and 3' primer sites (5'GGGAGTCCTACGTA-CAGTCTAG(N30)TCGATGCAGGATCTAGCTATC-GAT3'; SEQ ID NO.: 4) was used. The 5' and 3' primers to amplify the second pool comprise the sequences of 5'TAATACGACTCACTATAGGGAGTCCTACGTA-CAGTCTAG3' (SEQ ID NO. 5) and 5'ATCGATAGCTA-GATCCTGCATCGA3' (SEQ ID NO.: 6), respectively.

Two independent SELEX selections were carried to select clones that specifically bind to GPC3. Seven to nine rounds of nitrocellullose filter SELEX (Jhaveri et al., In vitro selection of RNA aptamers to a protein target by filter immobilization. *Curr Protoc Nucleic Acid Chem.* 2001, Chapter 9: Unit 9.3. doi: 10.1002/0471142700.nc0903s00. PMID: 18428881) were preformed using recombinant GPC3 protein. DNA clones from the final rounds of SELEX were sent for next generation sequencing and the data were analyzed for abundance. The highest abundant sequences (clones) were made via chemical synthesis and used in screening. The clones were screened for GPC3 binding via flow cytometry using engineered HEK293 cells overexpressing GPC3 (GPC3+ HEK293).

Example 2: Affinity Test of Anti-GPC3 Aptamer Candidates

Human hepatocellular Carcinoma cells HepG2 and Hep 3B overexpressing GPC3 were used to test the affinity of the selected positive clones. The binding studies indicate that several selected aptamer candidates (Table 3) from both libraries can bind human hepatocellular Carcinoma cells with high affinity.

TABLE 3 sequences of the selected anti-GPC3 aptamers

| Clone No. | SEQUENCE (5'-3') | SEQ ID NO |
|---|---|---|
| Common core sequence | CGZGTTGCTACZCRAG | 7 |
| W2.S4.1_R6F_6 | GGGAGACAAGAATAAAGCGAGTTGCTACTCAAGGCACGT CGTGTGCGCTGATTCAAGAGTCGATGATGCTTAGCTAG | 8 |
| W2.S4.1_R6F_10 | GGGAGACAAGAATAAAGCGAGTTTCGTGTCGTGTTGCTA CACAAGTCCGTTACCAAGAGTCGATGATGCTTAGCTAG | 9 |
| W2.S4.1_R6F_11 | GGGAGACAAGAATAAAGCGAGTTAACGGGTTGCTACCCA AGTCTTGCAATTCGCAAGAGTCGATGATGCTTAGCTAG | 10 |
| W2.S4.1_R6F_13 | GGGAGACAAGAATAAAGCGAGTTGCATGATCGTGTTGCTA CACGAGGTCTCATTAAGAGTCGATGATGCTTAGCTAG | 11 |
| W2.S4.1_R6F_14 | GGGAGACAAGAATAAAGCGAGTTTGAAGCCATTACCGGG TTGCTACCCAAGGACAAGAGTCGATGATGCTTAGCTAG | 12 |
| W2.S4.1_R6F_15 | GGGAGACAAGAATAAAGCGAGTTGTTGCATCGAGTTGCTA CTCAAGGTCGCGTCAAGAGTCGATGATGCTTAGCTAG | 13 |
| W2.S4.1_R6F_16 | GGGAGACAAGAATAAAGCGAGTTGCCTGTTGCATCGTGTT GCTACACAAGATTGAAGAGTCGATGATGCTTAGCTAG | 14 |
| W2.S4.1_R6F_17 | GGGAGACAAGAATAAAGCGAGTTCATCGTGTTGCTACACA AGGACTCTAGCACCAAGAGTCGATGATGCTTAGCTAG | 15 |
| W2.S4.1_R6F_19 | GGGAGACAAGAATAAAGCGAGTTGTTGACGGGTTGCTACC CGAGTCTTGCATTCAAGAGTCGATGATGCTTAGCTAG | 16 |
| JY-W2Ph2-S7R6F_R1_001_deep-S7; R = 9 | GGGAGTCCTACGTACAGTCTAGATCGGGTTGCTACCCAAG CTGCGGTACAAATCGATGCAGGATCTAGCTATCGAT | 17 |
| JY-W2Ph2-S7R6F_R1_001_deep-S13; R = 7 | GGGAGTCCTACGTACAGTCTAGGACGAGTTGCTACCCAAG TCCCGCGTTTGATCGATGCAGGATCTAGCTATCGAT | 18 |
| R9_JY-W1Ph2S7R9-S26; R = 40 | GGGAGTCCTACGTACAGTCTAGATCGGGTTGCTACCCAAG CTGCGGTTCAAATCGATGCAGGATCTAGCTATCGAT | 19 |
| R9_JY-W1Ph2S7R9-S341; R = 4 | GGGAGTCCTACGTACAGTCTAGATCGGGTTGCTACCCAAG CTGCGGTTCACATCGATGCAGGATCTAGCTATCGAT | 20 |
| R9_JY-W1Ph2S7R9-S544; R = 3 | GGGAGTCCTACGTACAGTCTAGATCGGGTTGCTACCCAAG CTGCGGTACAGATCGATGCAGGATCTAGCTATCGAT | 21 |
| R9_JY-W1Ph2S7R9-S69; R = 16 | GGGAGTCCTACGTACAGTCTAGATCGGGTTGCTACCCAAG CTGCGGTTCAGATCGATGCAGGATCTAGCTATCGAT | 22 |

Example 3: Characterization of Anti-GPC3 Aptamers

The aptamers with high GPC3 binding affinity were further aligned for sequence analysis. A common motif is identified among the selected anti-GPC3 aptamers. The conserved sequence among the identified anti-GPC3 aptamers comprises the sequence of CGZ$_3$GTTGCTACZ$_{12}$CRAG (SEQ ID NO.: 7), wherein Z at positions 3 and 12 form base pair (e.g., $Z_3$ is G/C and $Z_{12}$ is C/G; alternatively, $Z_3$ is A/T and $Z_{12}$ is T/A) and wherein R can be any nucleotide, A, T, G or C. The common sequence forms a conserved helix. Secondary structural analysis also indicates that the anti-GPC3 aptamers share a common structural folding as shown in FIG. 1. The folding includes two stems (Stem 1 and Stem 2) that are variable in size and nucleic acid sequences. The sequences of the double stranded stems 1 and 2 vary from each other. The double-stranded stem 1 may have any number of base pairs provided the base pairing is stable under suitable binding buffer conditions, e.g., 4 base pairs to 10 base pairs, or 4 base pairs, 5 base pairs, 6 base pairs, 7 base pairs, 8 base pairs, 9 base pairs or 10 base pairs. The results also indicate that complete deletion of the loops of stems 1 and 2 does not affect the binding affinity of the variant and its specificity to GPC3.

Example 4: Optimization of Anti-GPC3 Aptamers and Variants

Figure 3:
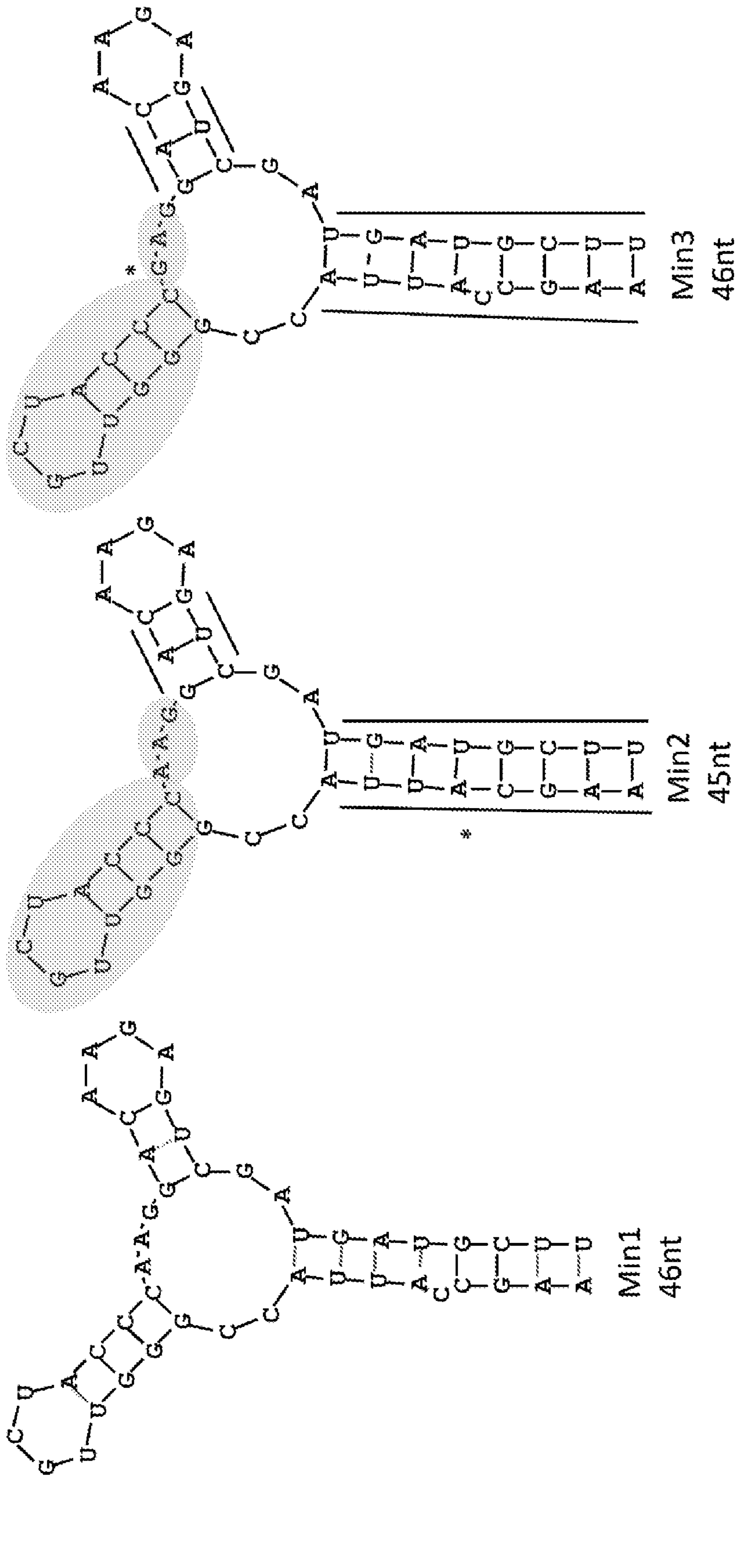
FIG. 3 shows the secondary structures of minimer variants. Figure discloses SEQ ID NOs.: 70-75, respectively, in order of appearance.
Figure 3:
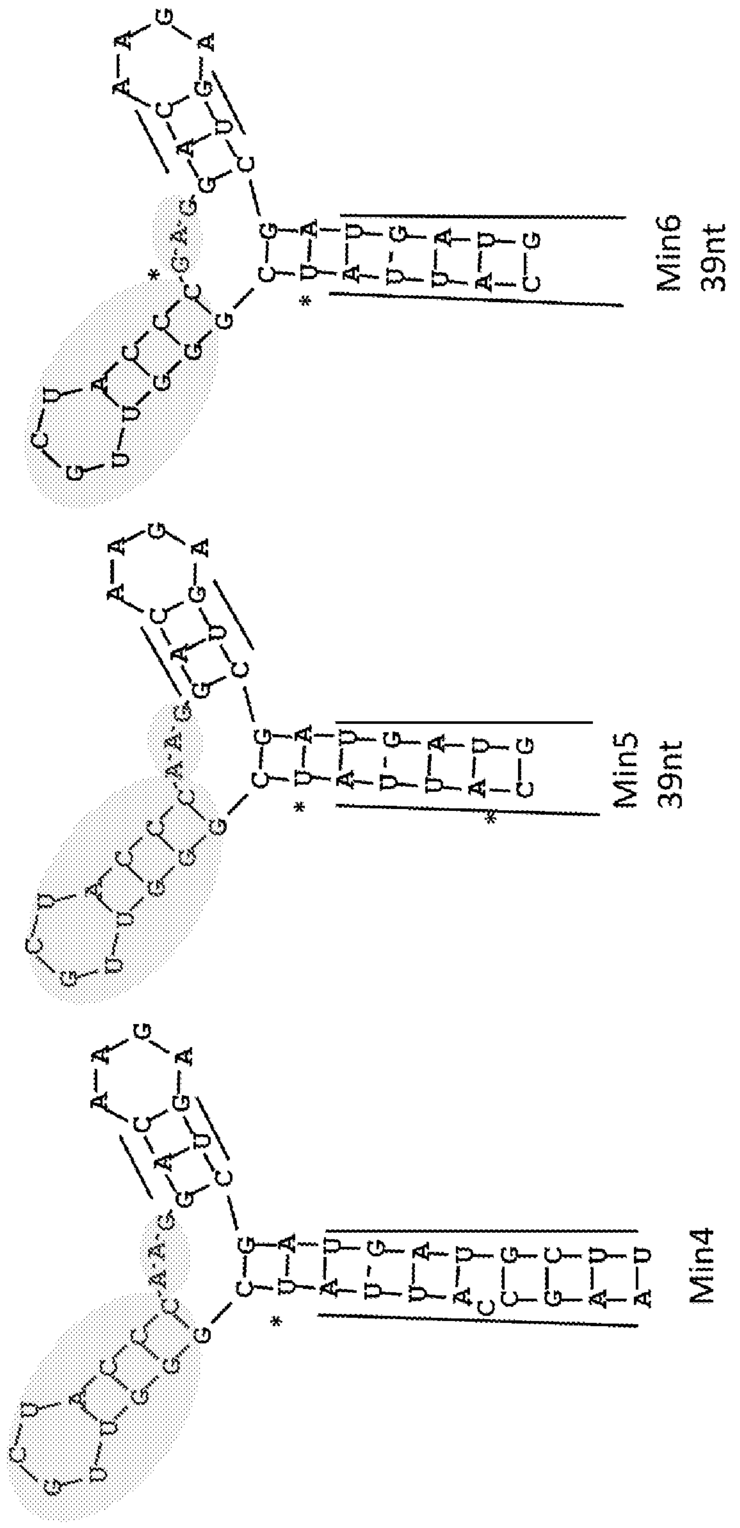

The full sequence from the positive clone W2.S4.1_R6F_14 (SEQ ID NO.: 12) was further optimized and truncated to minimize the aptamer sequence size. The variant sequences of the clone F14 (Table 4) modified the stem 1 region (FIG. 1). FIG. 3 demonstrates the secondary structures of these minimer variants. Each variant was tested for the binding affinity and specificity to GPC3 protein.

TABLE 4 variants of anti-GPC3 aptamer clone F14

| Variant | SEQUENCE (5'-3') | SEQ ID NO. |
|---|---|---|
| Min1 (46 nt) | AAGCCATTACCGGGTTGCTACCCAAGGACAAGAGTC GATGATGCTT | 26 |
| Min2 (45 nt) | AAGCATTACCGGGTTGCTACCCAAGGACAAGAGTCG ATGATGCTT | 27 |
| Min3 (46 nt) | AAGCCATTACCGGGTTGCTACCCGAGGACAAGAGTC GATGATGCTT | 28 |
| Min4 (46 nt) | AAGCCATTATCGGGTTGCTACCCAAGGACAAGAGTC GATGATGCTT | 29 |
| Min5 (39 nt) | CATTATCGGGTTGCTACCCAAGGACAAGAGTCGATG ATG | 30 |
| Min6 (39 nt) | CATTATCGGGTTGCTACCCGAGGACAAGAGTCGATG ATG | 31 |
| Min9 (39 nt) | CGTCATCGGGTTGCTACCCAAGGACAAGAGTCGATG ACG | 32 |
| Min9.2 (39 nt) | CGTCGTCGGGTTGCTACCCAAGGACAAGAGTCGACG ACG | 33 |
| Min11 (37 nt) | GGCATCGGGTTGCTACCCAAGGACAAGAGTCGATGC C | 34 |

The binding activities of variants Min 1, 2, 4 and 5, to GPC3$^+$ HEK293 cells were significantly increased as compared the full sequence of the clone F14 (Table 5). The results of these variants suggest that removal of excess sequences (e.g., sequences outside of the core common sequence), stabilizing base changes and/or removal of bulging bases can increase the affinity of a GPC3 aptamer to GPC3.

Binding of aptamer variants to GPC3 was tested with melting curve analysis (thermofluorimetric analysis). The control of experiment was carried out similarly with GPC3$^-$ HEK293 cells. The results indicate that the minimers with reduced size are more stable, e.g., the 39-mer (#Min9, #Min9.2 and #Min11) are thermally more stable than the original clone F14, #Min4 and #Min5.

TABLE 5

Stabilization of Stem 1 improves the GPC3 binding activity (MFI)

| | GPC3$^-$ HEK293 cells | GPC3$^+$ HEK293 cells |
|---|---|---|
| Clone F14 (SEQ ID NO. 12) | 1040 | 5050 |
| Min1 (SEQ ID NO. 26) | 579 | 11403 |
| Min2 (SEQ ID NO. 27) | 720 | 16652 |
| Min3 (SEQ ID NO. 28) | 444 | 377 |
| Min4 (SEQ ID NO. 29) | 1072 | 23261 |
| Min5 (SEQ ID NO. 30) | 946 | 19484 |
| Min6 (SEQ ID NO. 31) | 507 | 3619 |
| Min9 (SEQ ID NO. 32) | / | / |
| Min9.2 (SEQ ID NO. 33) | / | / |
| Min11 (SEQ ID NO. 34) | / | / |

Figure 2:
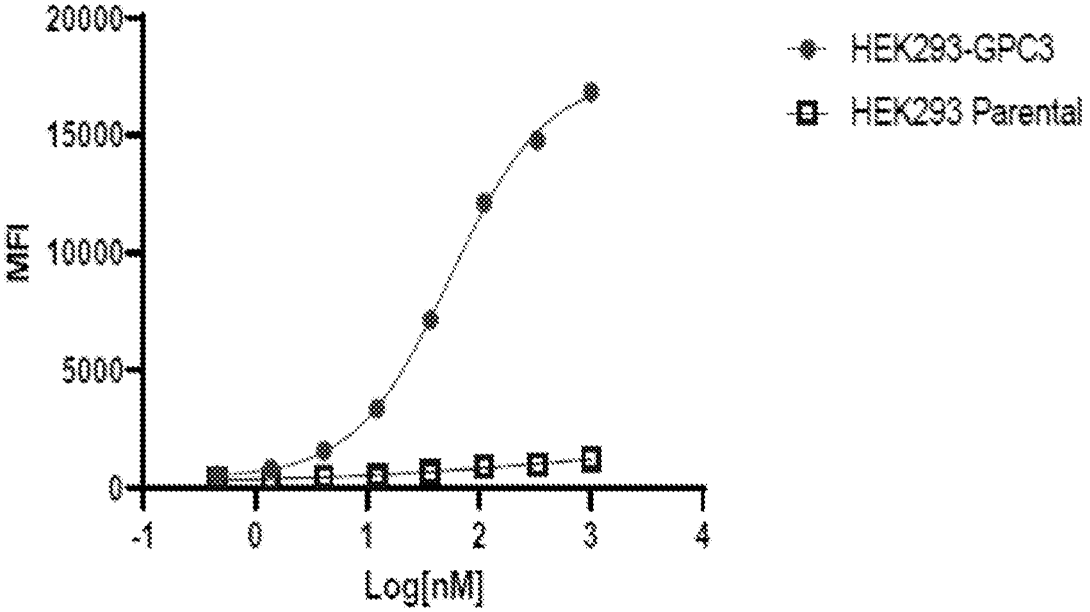
FIG. 2 demonstrates the binding affinity of a minimer variant of the clone F14 to endogenously expressed GPC3 protein.

The minimized variant #Min9 RNA aptamer (ID No.: GRX 8): 5' CGUCAUCGGGUUGCUACC-CAAGGACAAGAGUCGAUGACG3'; SEQ ID NO.: 23) demonstrates a high binding affinity to exogenously expressed GPC3 (FIG. 2). When the lineal GRX8 sequence is refolded, the binding activity of GRX8 improves. The activity is stable and not affected by the frequent freeze/thaw tests.

To further optimize the aptamer sequences and increase the GPC3 binding activity, GRX8 and other minimers were further mutated to identify sequence changes that resulted in improved GPC3 affinity. A pool of partial randomization sequences from GRX8 was created and selected by cell-SELEX using GPC3$^+$ HEK293 cells. Those variants comprise various changes to the structural elements of GRX8, including changes to the external loop, stack, helix, hairpin loop and stem, etc. The clones were further screened with Hep3B cells and minimized based on original structure. The minimer #Min9 was further randomly mutagenized for sequence changes that can improve the binding affinity to GPC3. Another minimer variant (ID No.: GRX46)

(5'CGUCAUCGGGUUGCUACCCAAGGUCAAGAGACGAUGACG3'; SEQ ID NO.: 24)

that is a variant derived from GRX8 demonstrates a similar, enhanced binding activity, and refolding behavior (data not shown). The best minimer, GRX46, as well as combinations of variants with top activities were selected for further evaluation (Table 6).

TABLE 6

Characteristics of top minimers

| | GRX8 | GRX46 | GRX8 with QUAD6 | GRX8 with triple | GRX49 |
|---|---|---|---|---|---|
| Ka (1/Ms) | 6.19E4 | 5.54E4 | $2.01 \times 10^5$ | $1.12 \times 10^5$ | $1.99 \times 10^5$ |
| Kd (1/s) | 7.32E−4 | 7.82E−4 | $2.48 \times 10^{-4}$ | $1.59 \times 10^{-4}$ | $1.46 \times 10^{-4}$ |
| KD (nM) | 13 | 15 | 1.24 | 1.41 | 0.74 |

The data indicate that three variants: GRX49 (5'CGUCAUCGGGUUGCUACCCAAGGCCAGGAGGCGAUGACG3'; SEQ ID NO. 25), GRX8 QUAD6 (5'CGUCAUCGGGUUGCUACCCAAGGUCAGGUGACGAUGACG3'; SEQ ID NO.: 35), and GRX8 triple 1 (5' CGUCAUCGGGUUGCUACCCAAGGUCAGGAGACGAUGACG3'; SEQ ID NO.: 36) do not require refolding for maximal activity (e.g., binding to Hep3B cells) (data not shown).

Additional variants surrounding the core motif were made in which stem 2 (as depicted in FIG. 1) is extended by 1 or 2 additional base pairs (GRX1187 and GRX2101 respectively) or replaced with an alternative stem and loop sequence (GRX958). Additionally, a construct was designed in which stem 2 is closed with a 4 base loop and stem 1 is open creating a new 5' and 3' end, GRX2102. All 4 of these constructs produce comparable folds and present the core motif in a similar fashion. The constructs were screened for GPC3 binding via flow cytometry using GPC3+ HEK293 cells and were shown to bind GPC3 with similar affinities. (Table 7)

TABLE 7

Kd of GPC3 aptamers

| | GRX49 | GRX958 | GRX1187 | GRX2101 | GRX2102 |
|---|---|---|---|---|---|
| Kd (nM) | 9.0 | 33.1 | 64.2 | 29.3 | 26.9 |

One positive variant GRX49

(5'CGUCAUCGGGUUGCUACCCAAGGCCAGGAGGCGAUGACG3'; SEQ ID NO. 25)

with increased activity was further tested. GRX49 can selectively bind to endogenously expressed GPC3 on different cancer cells, such as Hep3B, HepG2, NCI-H446, and Huh7 (data not shown).

The GPC3 aptamers were further tested for cancer cell targeting in vivo. $GPC3^+$Hep3B and $GPC3^-$A549 tumor cells were implanted into different nude mice. After implantation, mice were injected with FAM-labeled GRX8 at 0.45 mg/kg via tail vein. Fluorescent signal was specifically detected at Hep3B implanted tumors from 90 to 150 minutes post injection, but not at A549 implanted tumors. The results indicate the GPC3 aptamer can specifically target and accumulate at GPC3 positive cancer cells.

Example 5: In Vivo Evaluation of GPC3 Aptamer-Drug Conjugates

The GPC3 aptamer variant (#Min9) was conjugated with a drug DM1 using bispecific linker SMCC to form an aptamer-drug conjugate: DM1-CGTCATCGGGTTGCTACCCAAGGACAAGAGTCGATGACG (SEQ ID NO.: 32) (ID NO. #GRX26). GRX26 was tested in Hep3B xenograft mouse model for its activity in vivo (Table 8).

TABLE 8

Measurement of tumors after GRX26 administration

| Measurements | Vehicle | GRX26 (10 mg/kg) (IP/QD, 28 Days) | GRX26 (2.5 mg/kg) (28 Days) | Sorafenib Tosylate (10 mg/kg) (oral, QD/ 28 Days) |
|---|---|---|---|---|
| % of body weight loss | 3.36 | 14.86 | 10.67 | 4.54 |
| Relative tumor volume growth (Day 28) | 1.00 | 0.46 | 0.69 | 0.52 |

Figure 4:
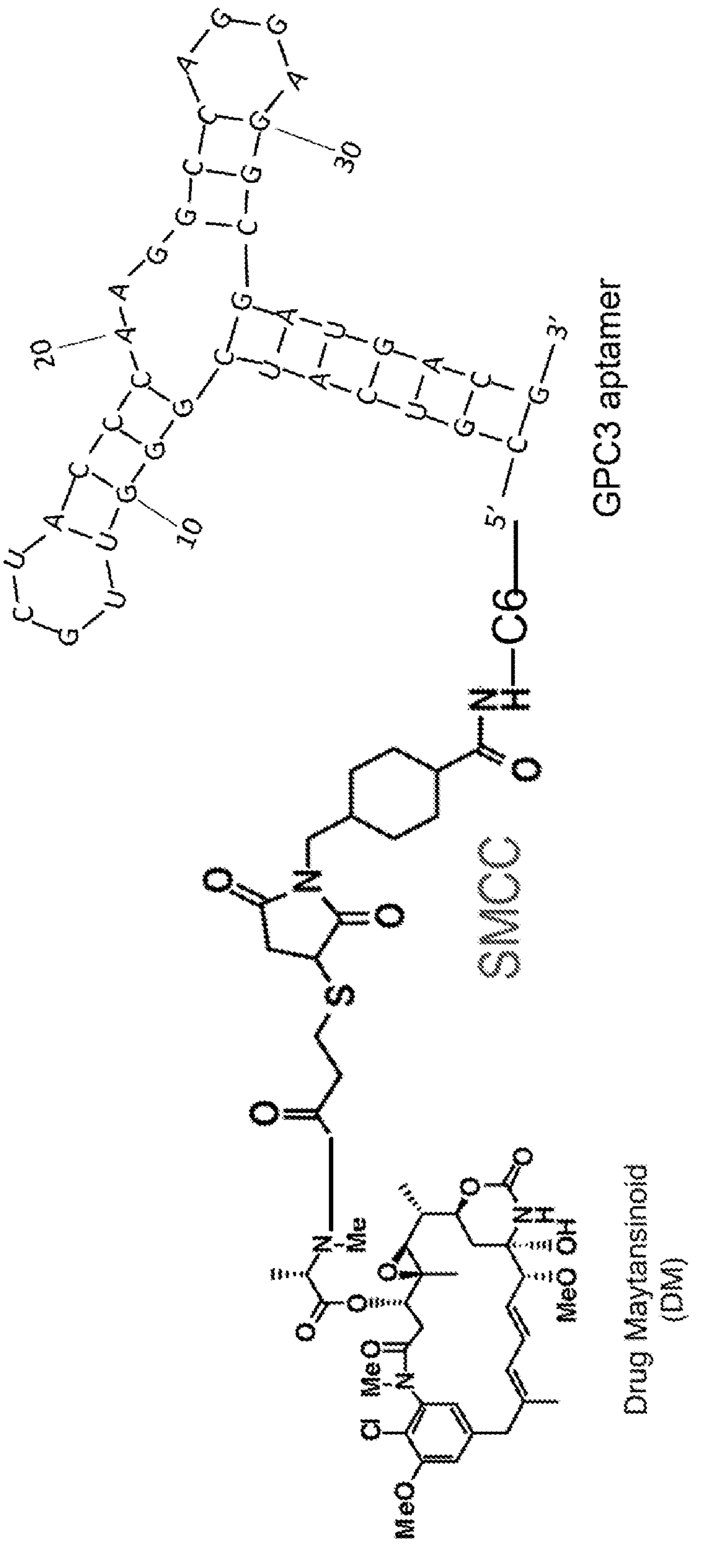
FIG. 4 depicts a GPC3 aptamer-DM drug conjugate. Figure discloses SEQ ID NO.: 23.

Example 6: GPC3 Aptamer-DM1 Conjugate (GRX54) to Target Tumor Killing Agents to Cancer Tissues A conjugate (GRX54) comprising a GPC3 aptamer (GRX49; SEQ ID NO.: 25) and DM1 was generated (FIG. 4). Drug Maytansinoid (DM1) is a membrane-permeable inhibitor of tubulin which can prevent cell division and eventually kill the cells.

Figure 5:
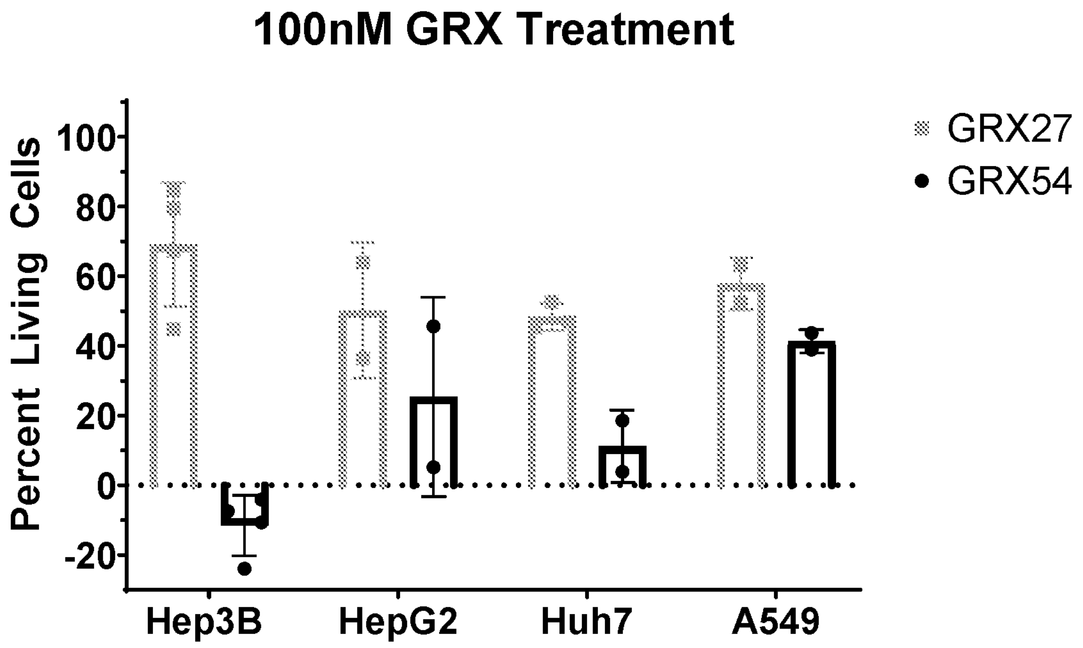
FIG. 5 is a histogram of the percentage of living cells post GRX54 treatment (100 nM). A scrambled version of the GPC3 aptamer GRX27 (100 nM) is used as a negative control.

The conjugate GRX54 shows specific binding activity to cells endogenously expressing GPC3 protein, including Hep3B and NCI-H446 cells. GRX54 can selectively kills $GPC3^+$ cells (FIG. 5).

The anti-tumor effect of GRX54 was tested in several tumor xenograft mouse models (Hep3B xenograft, Balb/c nude mice and NCI-H446 xenograft, Balb/c nude mice). GRX54 was administered to mice at different doses via intraperitoneal injection (IP). For each group, mice were administered with vehicle, or GRX54 once a day (QD) for 3, 5 or 7 days. Tumor growth was measured. An anti-cancer drug Sorafenib Tosylate (30 mg/kg, oral administration, once a day) (Hep3B xenograft mouse model) or irinotecan (40 mg/kg, i.p. twice a day for 4 days) (NCI-H446 xenograft mouse model) were used as positive controls.

TABLE 9

Measurements of tumor growth after GRX54 treatment

| Measurements | Hep3B Xenograft, Balb/c nude mice<br>Vehicle (IP, QD) | GRX54 (10 mg/kg) (IP, QD/7 Days on/7 days off for 28 days) | GRX54 (10 mg/kg) (IP, QD/5 Days on/9 days off for 28 days) | GRX54 (10 mg/kg) (IP, QD/3 Days on/4 days off for 28 days) | Sorafenib Tosylate (30 mg/kg) (oral, QD 28 days) |
|---|---|---|---|---|---|
| % of body weight loss (Day 28) | 10.27 | 12.69 | 11.49 | 13.91 | 9.33 |
| Relative tumor volume growth (Day 28) | 1.00 | 0.57 | 0.55 | 0.68 | 0.38 |

TABLE 10

Measurements of tumor growth after GRX54 treatment

| Measurements | NCI-H446 xenograft, Balb/c nude mice<br>Vehicle (IP, QD) | GRX54 (10 mg/kg) (IP, QD/7 Days on/7 days off for 28 days) | GRX54 (10 mg/kg) (IP, QD/5 Days on/9 days off for 28 days) | Irinotecan (40 mg/kg) (I.P. QD for 28 days) |
|---|---|---|---|---|
| % of body weight loss (Day 29) | −19.74 | −1.83 | −12.20 | −5.29 |
| Relative tumor volume growth (Day 29) | 1.00 | 0.10 | 0.55 | −0.04 |

The data indicate that the GPC3 aptamer can specifically target GPC3 expressing cells in vitro and in vivo (data not shown). GRX54 is capable of selectively killing a variety of GPC3 expressing liver cells in vitro. The anti-tumor effect of GRX54 is shown in the tumor xenograft mouse models: Hep3B xenograft, Balb/c nude mice and NCI-H446 xenograft, Balb/c nude mice. GRX54 decreases Hep3B tumor volume in a Balb/c nude mouse xenograft model by ~30-45% depending on treatment schedule and NCI-H446 tumor volume by ~45-90% depending on treatment schedule (Tables 9 and 10). The data show that GRX54 is a novel GPC3-targeting molecule capable of reducing tumor size with IP injection.

Example 7: GRX51 (GPC3 Aptamer-CpG7909 Fusion) Stimulates Immune Response

Figure 6A:
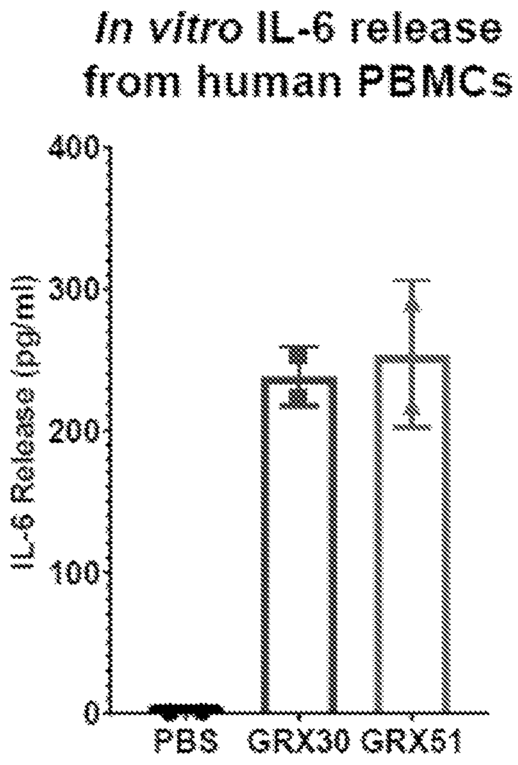
FIG. 6A is a histogram demonstrating IL-6 release from PBMCs after GRX51 stimulation.
Figure 6B:
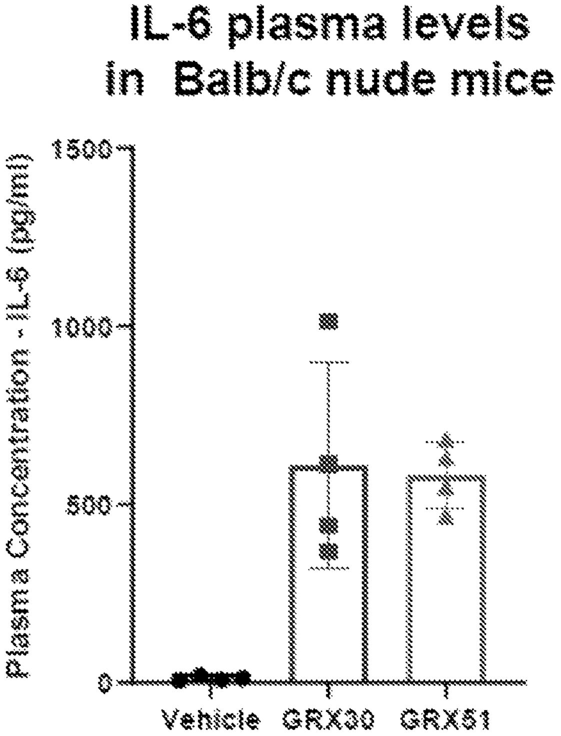
FIG. 6B a histogram demonstrating IL-6 plasma levels in Balb/c nude mice after GRX51 stimulation. Unconjugated CpG is used as positive control in both experiments (GRX30).

A fused oligonucleotide (GRX51) (5' dTsdCsdGsdTsdCsdGsdTsdTsdTsdGsdTsdCsdGsdTsd TsdTsdTsdGsdTsdCsdGsdTsdTm CmGmUmCmA-mUmCmGmGmGmUmUmGmCmUmAmCmCmCmA-mAmGmGmCmCm AmGmGmAmGmGmCmGmA-mUmGmAmCmG3'; SEQ ID NO.: 68) comprising a GPC3 aptamer-GRX49 and pS linked CpG7909 (5'dTsdCsdGsdTsdCsdGsdTsdTsdTsdTsdGsdTsdCsdGsd TsdTsdTsdTsdGsdTsdCsdGsdTsd T3'; SEQ ID NO.: 67) was generated. CpG7909 (5' TCGTCGTTTTGTCGTTTTGTCGTT3'; SEQ ID NO. 66) is an unmethylated CpG aptamer that acts as an immunostimulatory TLR9 agonist. The binding activity test shows that the fusion of two oligonucleotide sequences does not affect the binding activity of GRX51 to GPC3 protein. A comparable IC50 (32.74 nM) was achieved as compared to the GPC3 aptamer alone (Table 6). A functionality test also demonstrates that fusion does not affect the immunomodulatory function of CpG7909. As shown in FIGS. 6A and 6B, GRX51 treatment stimulates IL-6 release in vitro in human PBMCs and in vivo in Balb/c nude mice similarly to CpG treatment alone (#GRX30 in FIGS. 6A and 6B).

The immunostimulatory effects of CpG7909 can enhance anti-tumor activity. Xenograft mouse models of human hepatic cell lines (Hep3B xenograft, Balb/c nude mice; Hep3B xenograft, CD34+ humanized mice) were used to test the anti-tumor activity of the fusion conjugate GRX51. GRX51 was administered to mice at different doses via intraperitoneal injection (IP). For each group, mice were treated with vehicle, CpG7909, or GRX51 once a day (QD) for 7 days. Tumor growth was measured on Day 7 and Day 18 (Table 11). An anti-cancer drug Sorafenib Tosylate was used as a positive control.

TABLE 11

| Measurements of tumor growth after GRX51 treatment | | | | |
|---|---|---|---|---|
| | Hep3B Xenograft, Balb/c nude mice | | | |
| Measurements | Vehicle (IP, QD/ 7 Days) | CpG (5 mg/kg) (IP, QD/ 7 Days) | GRX51 (10 mg/kg) (IP, QD/ 7 Days) | Sorafenib Tosylate (10 mg/kg) (oral, QD/ 14 Days) |
| % of body weight loss (Day 7) | 1.80 | 11.25 | 9.33 | 5.27 |
| Relative tumor volume growth (Day 7) | 1.00 | 0.57 | 0.73 | 0.96 |
| Relative tumor volume growth (Day 18) | 1.00 | 0.47 | 0.57 | 0.80 |

Figure 7:
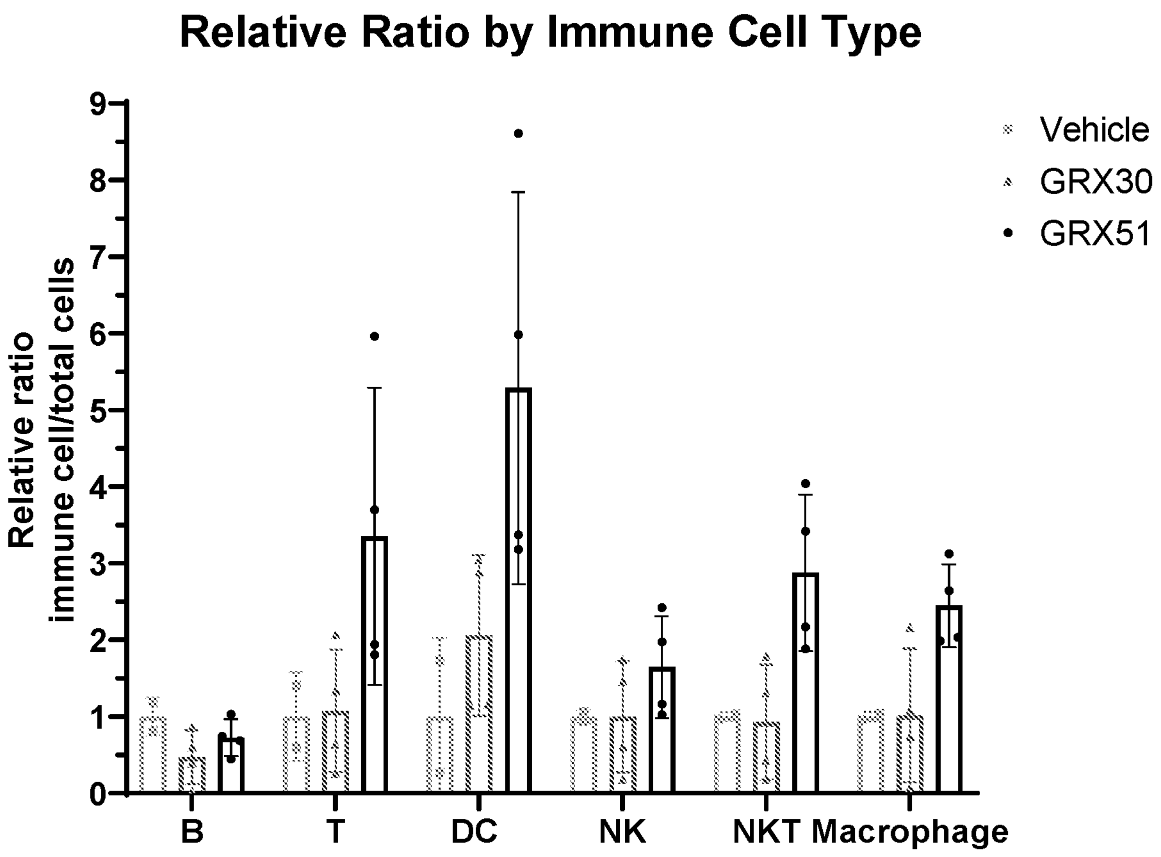
FIG. 7 is a histogram demonstrating the relative ratio of immune cells within GRX51 stimulated tumors. CpG7909 (#GRX30) is used as control.

At the end of the study, tumor tissues from each group were analyzed for immune cell populations by FAC Sorting. Active immune cells are significantly increased in GRX51 stimulated tumors. The intra-tumoral ratios of macrophages, T lymphocytes, dendritic cells and natural killer T cells increase within the tumor, while the intra-tumoral ratio of B lymphocytes is decreased (FIG. 7).

The data indicate that systemic administration through intra peritoneal (i.p.) injection of GRX51 decreases Hep3B tumor volume in a Balb/c nude mouse xenograft model by ~30-50% depending on treatment schedule, while also increasing immune cell infiltration. Final tumor volumes of GRX51 treated animals are consistent with tumor volumes of animals treated with the standard of care compound, sorafenib tosylate. Due to its GPC3-targeting capacity, systemic dosing of GRX51 (15 mg/kg) is less toxic than systemic administration with equimolar amounts of CpG 7909 alone (5 mg/kg), with a comparable effect on tumor shrinkage. While both GRX51 and CpG 7909 induce immune cell recruitment, GRX51 treated mice had a final immune:tumor cell ratio of 2.45±0.56, while CpG 7909-treated animals had a ratio of 1.51±0.95 relative to the vehicle control after a 7-day on/7-day off daily dosing schedule.

The results indicate that the anti-GPC3 aptamer can selectively target CpG7909 to tumor tissue, thereby recruiting immune cells to the tumor. The recruited and activated immune cells can kill tumor cells and inhibit tumor growth.

The targeting and anti-tumor function of GRX51 was further investigated using a Hep3B xenograft, CD34+ humanized mouse model.

TABLE 12

| Measurements of tumor growth after GRX51 treatment | | | | | | |
|---|---|---|---|---|---|---|
| | Hep3B Xenograft, CD34 + humanized mice | | | | | |
| Measurements | Vehicle | GRX51 (7.5 mg/kg) (21 Days) | GRX51 (2.5 mg/kg) (21 Days) | GRX51 (2.5 mg/kg) + Keytruda 10 mg/kg (21 Days) | GRX51 (2.5 mg/kg) + Keytruda 10 mg/kg (21 Days) | Keytruda 10 mg/kg |
| % of body weight loss | 1.85 | 10.11 | 8.01 | 10.55 | 5.06 | 3.66 |
| Relative tumor volume growth (Day 11) | 1.00 | 0.67 | 1.02 | 0.37 | 0.94 | 0.82 |

The results in the Hep3B xenograft in CD34+ humanized mice also showed GRX51 primes tumors for combination treatments with the PD-1R inhibitor Keytruda. Mice were treated with GRX51 (7.5 mg/kg daily i.p. dose, 11 days), the PD-1R inhibitor Keytruda (10 mg/kg once every 3 days i.p., 11 days), or a combination of the two drugs. The GRX51 treatment alone outperformed Keytruda alone, reducing tumor size by 33% and 18% respectively. Notably, the combination of GRX51 with Keytruda reduced tumor size by 63% (Table 12). Together, our data show that GRX51 is a novel GPC3-targeting molecule capable of reducing tumor size and priming GPC3-positive tumors for combination immunotherapy, without inducing major systemic toxicity with i.p. injection.

The invention claimed is:

1. An oligonucleotide that binds to GPC3 wherein the oligonucleotide comprises a nucleic acid sequence selected from the group consisting of SEQ ID NOs: 8-36 and 76-79.

2. The oligonucleotide of claim 1 wherein the oligonucleotide comprises at least one 2'-O-methylated (2'OME) nucleotide.

3. The oligonucleotide of claim 2 wherein the oligonucleotide comprises a nucleic acid sequence selected from the group consisting of SEQ ID NOs: 37-65 and 80-83.

4. An immunostimulatory aptamer chimera comprising a targeting aptamer that binds the chimera to a cell-specific surface protein and an immunostimulatory molecule that induces an immunostimulatory activity in the target cell, wherein the targeting aptamer is a GPC3 aptamer that specifically binds to the GPC3 protein on the surface of the target cell, and wherein the GPC3 aptamer comprises a nucleic acid sequence selected from the group consisting of SEQ ID NOs: 8-65 and 76-83.

5. The immunostimulatory aptamer chimera of claim 4 wherein the molecule which induces the immunostimulatory function is an unmethylated CpG immunostimulatory oligonucleotide.

6. The immunostimulatory aptamer chimera of claim 5 wherein the CpG immunostimulatory oligonucleotide is CpG7909 having a sequence of presented by SEQ ID NO: 66, or SEQ ID NO: 67.

7. The immunostimulatory aptamer chimera of claim 4 wherein the chimera comprising a nucleic acid sequence of SEQ ID NO: 68 (GRX51) that activates immune cells in a tumor tissue.

8. An aptamer conjugate comprising a GPC3 aptamer that is conjugated with a functional moiety, wherein the GPC3 aptamer comprises a nucleic acid sequence selected from the group consisting of SEQ ID NOs: 8-65 and 76-83.

9. The aptamer conjugate of claim 8 wherein the functional moiety is an anti-cancer drug and wherein the anti-cancer drug is selected from the group consisting of Drug Maytansinoid (DM1), a cancer immunotherapeutic agent, and a multi-kinase inhibitor that is selected from the group consisting of sorafenib, lenvatinib, cabozantinib, ramucirumab, sunitinib, linifanib, brivanib, tivantinib, and everolimus.

10. The aptamer conjugate of claim 9 wherein the drug is DM1.

11. The aptamer conjugate of claim 9 wherein the cancer immunotherapeutic agent is an immunomodulator, a cancer vaccine, an immunomodulatory antibody or a functional fragment thereof, or an immunostimulatory cell.

12. A method of stimulating an immune response in a tumor tissue comprising delivering the immunostimulatory aptamer chimera of claim 4 to the tumor tissue.

13. The method of claim 12 wherein the immunostimulatory aptamer chimera comprises an unmethylated CpG immunostimulatory oligonucleotide CpG7909 having a nucleic acid sequence of SEQ ID NO: 66, or SEQ ID NO: 67.

14. The method of claim 13 wherein the immunostimulatory aptamer chimera comprises a nucleic acid sequence of SEQ ID NO: 68 (GRX51).

* * * * *